(12) United States Patent
Okubo et al.

(10) Patent No.: US 10,457,705 B2
(45) Date of Patent: Oct. 29, 2019

(54) CARRIER FOR LIGAND IMMOBILIZATION

(71) Applicant: KANEKA CORPORATION, Osaka-shi (JP)

(72) Inventors: Takahiro Okubo, Takasago (JP); Yoshikazu Kawai, Takasago (JP); Masaru Hirano, Takasago (JP); Fuminori Konoike, Takasago (JP); Keiichi Karasugi, Takasago (JP); Tatsuya Honda, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 16/227,688

(22) Filed: Dec. 20, 2018

(65) Prior Publication Data
US 2019/0256555 A1 Aug. 22, 2019

Related U.S. Application Data

(62) Division of application No. 15/025,152, filed as application No. PCT/JP2014/075740 on Sep. 26, 2014, now Pat. No. 10,221,211.

(30) Foreign Application Priority Data

Sep. 27, 2013 (JP) ................................. 2013-202007
Oct. 8, 2013 (JP) ................................. 2013-211453

(51) Int. Cl.

| B01J 20/24 | (2006.01) |
|---|---|
| C07K 1/22 | (2006.01) |
| B01J 20/30 | (2006.01) |
| C08B 1/08 | (2006.01) |
| C08B 15/08 | (2006.01) |
| C08B 15/10 | (2006.01) |
| C08B 3/06 | (2006.01) |
| C07K 16/00 | (2006.01) |
| B01J 20/26 | (2006.01) |
| B01J 20/285 | (2006.01) |
| C08J 3/16 | (2006.01) |
| B01J 20/28 | (2006.01) |
| B01J 20/32 | (2006.01) |
| B01J 20/286 | (2006.01) |
| B01D 15/38 | (2006.01) |
| C08L 1/12 | (2006.01) |
| C08L 1/04 | (2006.01) |
| C08L 1/02 | (2006.01) |
| C08B 16/00 | (2006.01) |
| C08B 15/00 | (2006.01) |
| C08J 9/00 | (2006.01) |

(52) U.S. Cl.
CPC ............ *C07K 1/22* (2013.01); *B01D 15/3809* (2013.01); *B01J 20/24* (2013.01); *B01J 20/267* (2013.01); *B01J 20/28004* (2013.01); *B01J 20/285* (2013.01); *B01J 20/286* (2013.01); *B01J 20/28016* (2013.01); *B01J 20/3071* (2013.01); *B01J 20/3085* (2013.01); *B01J 20/3212* (2013.01); *B01J 20/3219* (2013.01); *B01J 20/3274* (2013.01); *B01J 20/3293* (2013.01); *C07K 16/00* (2013.01); *C08B 1/08* (2013.01); *C08B 3/06* (2013.01); *C08B 15/005* (2013.01); *C08B 15/08* (2013.01); *C08B 15/10* (2013.01); *C08B 16/00* (2013.01); *C08J 3/16* (2013.01); *C08J 9/00* (2013.01); *C08L 1/02* (2013.01); *C08L 1/04* (2013.01); *C08L 1/12* (2013.01); *B01J 2220/52* (2013.01); *C08J 2301/02* (2013.01); *C08J 2301/04* (2013.01); *C08J 2301/12* (2013.01); *C08L 2205/18* (2013.01)

(58) Field of Classification Search
CPC ............... B01J 20/24; B01J 20/28004; B01J 20/28016; B01J 20/285; B01J 20/286; B01J 20/3071; B01J 20/261; B01D 15/38; B01D 15/3809; C08B 1/08; C07K 1/22
USPC ...................................................... 502/439
See application file for complete search history.

(56) References Cited

U.S. PATENT DOCUMENTS

| 6,602,990 B1 | 8/2003 | Berg |
|---|---|---|
| 2003/0012941 A1 | 1/2003 | Fujita et al. |
| 2003/0186041 A1 | 10/2003 | Fujita et al. |
| 2008/0070027 A1 | 3/2008 | Fujita et al. |
| 2008/0241536 A1 | 10/2008 | Luo et al. |
| 2009/0062118 A1 | 3/2009 | Umeda et al. |
| 2013/0331563 A1 | 12/2013 | Kawai et al. |

(Continued)

FOREIGN PATENT DOCUMENTS

| CA | 2 828 369 A1 | 9/2012 |
|---|---|---|
| EP | 0 750 007 A1 | 12/1996 |

(Continued)

OTHER PUBLICATIONS

Extended European Search Report dated Jan. 8, 2019 in European Patent Application No. 18199393.2, citing documents therein, 7 pages.

(Continued)

*Primary Examiner* — Edward M Johnson
(74) *Attorney, Agent, or Firm* — Oblon, McClelland, Maier & Neustadt, L.L.P.

(57) ABSTRACT

A carrier for ligand immobilization obtained by shrinking polysaccharide porous beads not less than 10% by a shrinkage rate defined by the following formula, and crosslinking the polysaccharide porous beads: Shrinkage rate (%)=(1−$V_2/V_1$)×100 (wherein, $V_1$ indicates the gel volume of polysaccharide porous beads before shrinkage, and $V_2$ indicates the gel volume of polysaccharide porous beads after shrinkage).

20 Claims, 3 Drawing Sheets
Specification includes a Sequence Listing.

(56) References Cited

U.S. PATENT DOCUMENTS

2014/0128253 A1     5/2014   Umeda et al.
2015/0297820 A1    10/2015   Kawai et al.

FOREIGN PATENT DOCUMENTS

| JP | 1 278534 | 11/1989 |
| JP | 11 158202 | 6/1999 |
| JP | 2000 508361 | 7/2000 |
| JP | 2008 248466 | 10/2008 |
| JP | 2008 279366 | 11/2008 |
| JP | 2009 242770 | 10/2009 |
| WO | WO 02/057319 A2 | 7/2002 |
| WO | WO 02/057319 A3 | 7/2002 |
| WO | 2012 121258 | 9/2012 |
| WO | 2014 038686 A1 | 3/2014 |

OTHER PUBLICATIONS

Ishimura, D., et al., "Influences of chemical modifications on the mechanical strength of cellulose beads", Cellulose. vol. 5. No. 2, XP055537785A, Jun. 1, 1998, pp. 135-151.

Yu, C., et al., "Immobilization Staphylococcal Protein A on Magnetic Cellulose Microspheres for IgG Affinity Purification", Artificial Cells, Blood Substitutes, and Biotechnology, Marcel Dekker Inc., US., vol. 35, No. 5. XP008142436, Jan. 1, 2007, pp. 467-480.

International Search Report dated Dec. 22, 2014 in PCT/JP2014/075740 filed Sep. 26, 2014.

Extended European Search Report dated Jan. 17, 2017 in Patent Application No. 14849556.7.

[Figure 1]
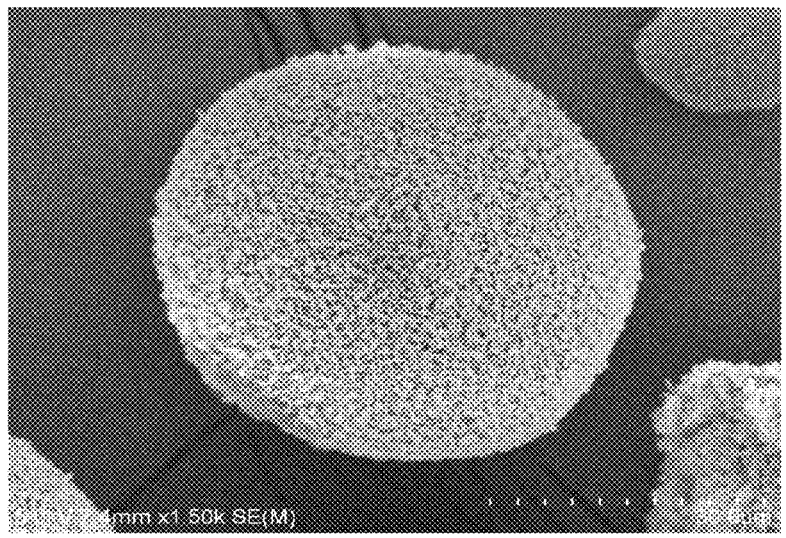
[Figure 2]
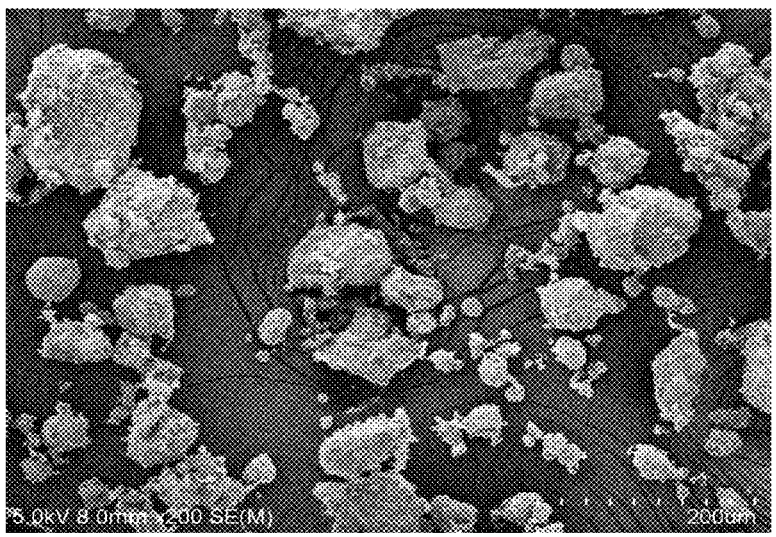

[Figure 3]
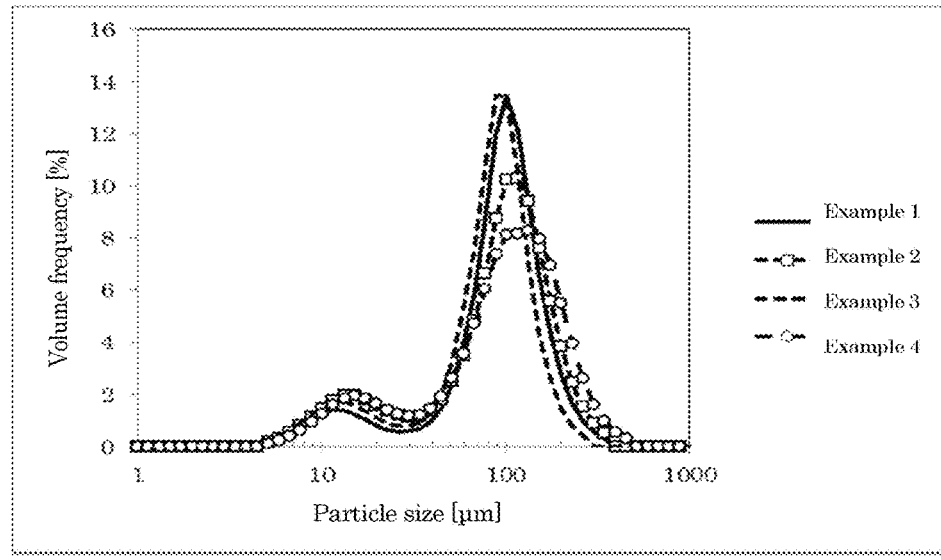
[Figure 4]
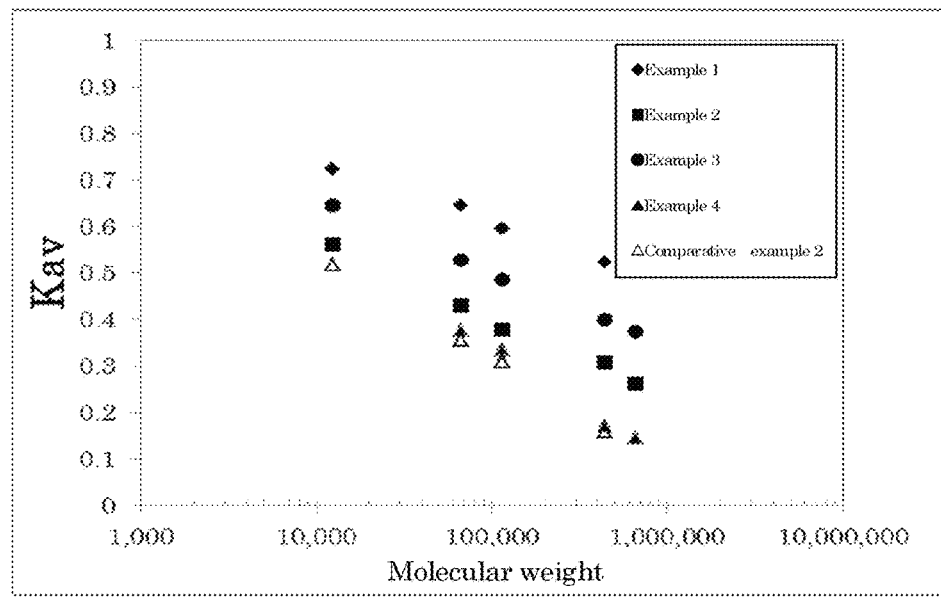

[Figure 5]
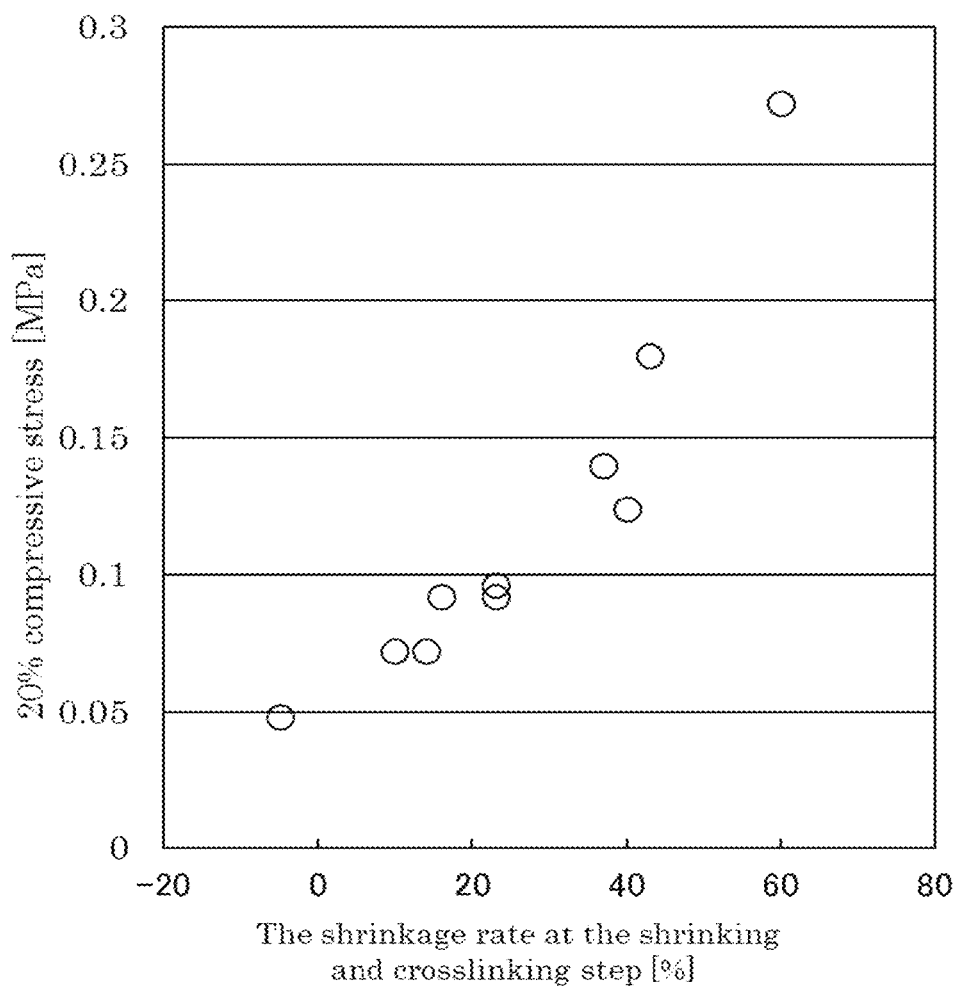

CARRIER FOR LIGAND IMMOBILIZATION

CROSS REFERENCES TO RELATED APPLICATIONS

This application is a divisional of U.S. patent application Ser. No. 15/025,152, filed on Mar. 25, 2016, which is a National Stage Entry of International Application No. PCT/JP14/75740, filed on Sep. 26, 2014, the disclosures of which are incorporated herein by reference in their entireties. This application claims priority to Japanese Patent Application No. 2013-211453 filed on Oct. 8, 2013, and Japanese Patent Application No. 2013-202007, filed on Sep. 27, 2013, the disclosures of which are incorporated herein by reference in their entireties.

TECHNICAL FIELD

In the first embodiment, the present invention relates to a process for producing porous cellulose beads, and more specifically, to a process for producing porous cellulose beads utilizing liquid-liquid dispersion. Also, in the second embodiment, the present invention relates to a carrier for ligand immobilization comprising polysaccharide porous beads, and to an adsorbent using the same.

BACKGROUND ART

(1) Regarding Porous Cellulose Beads (First Embodiment)

Cellulose is resistant to acid and basic solvents, and various substituents can be added to cellulose by modifying the cellulose. Therefore, cellulose porous beads have been used as adsorbents for various substances (Patent Documents 1, 2).

Very few solvents can dissolve cellulose, and cellulose porous particles are produced, generally by dissolving cellulose in a highly toxic solvent such as calcium thiocyanate. However, for producing cellulose porous beads by the production method as described above, the handling is difficult in terms of corrosiveness and safety, and it is the current state of art that providing equipment thereof is not easy.

Meanwhile, ion liquids, which are nonvolatile and have the property of assuming liquid in a wide temperature range, attract attentions in recent years. Ion liquids are mainly applied as functional solvents, solvents for an ionics device and tissue-derived biomaterials such as polypeptide. Recently, ion liquids are found to dissolve cellulose, and are applied, for example, in production of fibers (Patent Document 3). However, ion liquids are expensive, and it is not easy to form cellulose in a low-cost method.

Under these circumstances, a process for forming cellulose beads in a low-cost and simple process has been reported (Patent Document 4). However, Patent Document 4 lacks description of a specific process for controlling the pore size, particle diameter and the like of cellulose beads. Therefore, further improvement should be made for using it as an adsorbent or the like for various substances.

(1) Regarding Carrier for Ligand Immobilization (Second Embodiment)

As described above, porous cellulose beads have a room for improvement regarding the production process thereof. In addition, polysaccharide porous beads including such porous cellulose beads have a problem to be solved in production of a carrier for ligand immobilization using the same. That is, polysaccharide porous beads are useful as a carrier for ligand immobilization, and for example, Non-patent Document 1 teaches immobilizing an affinity ligand to a carrier of porous cellulose beads and using them as an adsorbent. The polysaccharide porous beads on which ligands are immobilized are generally packed in a column, and an object to be treated is allowed to run through the column, and thus the objective matter is adsorbed. However, when the strength of the carrier for ligand immobilization is low, problems such as critical compression of the carrier due to liquid feeding pressure, and increase in pressure loss arise. In particular, since the operation pressure increases with the column scale and the linear velocity, increase in strength of a carrier for ligand immobilization is strongly demanded.

As a method for increasing the strength of a carrier for ligand immobilization, a method of cross linking polysaccharide porous beads is known. For example, Patent Document 5 increases the strength by crosslinking a carrier of cellulose-based beads, and Patent Document 6 increases the strength by crosslinking a carrier of agarose-based beads.

It goes without saying that a carrier for ligand immobilization desirably has excellent adsorption after immobilization of a ligand, as well as having increased strength.

PRIOR ART DOCUMENTS

Patent Documents

Patent Document 1: JP-A-1-278534
Patent Document 2: JP-A-11-158202
Patent Document 3: JP-A-2008-248466
Patent Document 4: WO2012/121258
Patent Document 5: JP-A-2008-279366
Patent Document 6: JP-W-2000-508361

Non-Patent Document

Non-patent Document 1: "Affinity Chromatography", attributed to Kenichi Kasai et al., Tokyo Kagaku Dozin, 1991

SUMMARY OF THE INVENTION

Problems to be Solved by the Invention

In the case of the first embodiment (improvement in porous cellulose beads), it is an object of the present invention to provide a process for producing porous cellulose beads that can be used as an adsorbent for various substances stably and conveniently without using a highly toxic solvent such as calcium thiocyanate, and controlling the bead characteristics of the cellulose beads.

In the case of the second embodiment (improvement in carrier for ligand immobilization), it is an object of the present invention not only to improve the strength but also to maintain and improve the adsorption by a ligand in using polysaccharide porous beads as a carrier for ligand immobilization.

Solutions to the Problems

1. In the Case of the First Embodiment
(Improvement in Porous Cellulose Beads)

Through diligent efforts in light of the problem of the first embodiment (improvement in porous cellulose beads), the inventors of the present application found that the aforementioned problems are solved in the manner of the later-described invention (1), and eventually completed the invention according to the first embodiment (improvement in porous cellulose beads). The later-described invention (2) and the following inventions may be preferred.

(1) A process for producing porous cellulose beads, comprising the steps of:
  a) mixing an alkali aqueous solution and cellulose to prepare a cellulose micro dispersion at low temperature,
  b) adding water to the cellulose micro dispersion to prepare a cellulose slurry, and
  d) bringing the cellulose slurry into contact with a coagulation solvent.

(2) The process according to (1), further comprising the step of:
  c) raising the temperature of the cellulose slurry, after the step b),
  wherein the step d) is conducted after the step c).

(3) The process according to (1) or (2), wherein an alkali concentration of the cellulose micro dispersion is not less than 8 wt % and not more than 10 wt %.

(4) The process according to any one of (1) to (3), wherein an alkali concentration of the cellulose slurry is not less than 5 wt %.

(5) The process according to any one of (1) to (4), wherein the temperature at which the cellulose slurry is prepared is not less than 4° C. and not more than 20° C.

(6) The process according to any one of (1) to (5), wherein after liquid-liquid dispersing the cellulose slurry in a water-insoluble liquid which is a dispersion medium to prepare droplet, the liquid-liquid dispersion is brought into contact with a coagulation solvent.

(7) The process according to any one of (1) to (6), wherein concentration of the cellulose in the cellulose slurry is 1-7 wt %.

(8) The process according to any one of (1) to (7), wherein the cellulose is either regenerated cellulose, crystalline cellulose, microcrystalline cellulose, or cellulose acetate.

(9) The process according to (8), wherein a degree of polymerization of the cellulose is not more than 1000.

(10) The process according to any one of (1) to (9), wherein the water-insoluble liquid is dichlorobenzene, hexane, ethyl acetate, straight-chain saturated fatty acid having 6 to 12 carbons, unsaturated fatty acid having 16 to 24 carbons, animal fats and vegetable oils having a melting point of not more than 100° C., hydrogenated animal fats and vegetable oils, fractionated oil prepared by fractionating and purifying a high-melting point fraction of animal fats and vegetable oils or hydrogenated animal fats and vegetable oils, unsaturated fatty acid triglycerides, edible waxes, fats and oils from microalgae, fats and oils from microorganisms, medium-chain fatty acid triglycerides, or unsaturated fatty acid triglycerides.

(11) The process according to any one of (1) to (9), wherein the coagulation solvent contains alcohols or glycols.

(12) The process according to (11), wherein the alcohols is at least one selected from the group consisting of isobutanol, 2-butanol, sec-butanol, 2-methyl-2-propanol, 1-propanol, 2-propanol, ethanol, and methanol.

(13) The process according to (11), wherein the glycols is at least one selected from the group consisting of glycerol, ethylene glycol, and propylene glycol.

(14) Porous cellulose beads produced by the process according to any one of (1) to (13), wherein the porous cellulose beads have an exclusion limit molecular weight of $1.0 \times 10^6$ to $1.0 \times 10^{11}$.

(15) The porous cellulose beads according to (14), wherein the porous cellulose beads have a median particle diameter of 50 μm to 100 μm.

2. In the Case of the Second Embodiment (Improvement in Carrier for Ligand Immobilization)

Through diligent efforts for solving the problem of the second embodiment, the inventors of the present application unexpectedly found that a specific strength improving means not only increases the strength of the carrier, but also maintains and improves the adsorption by a ligand. To be more specific, inventors found that by subjecting polysaccharide porous beads to a shrinking treatment, the compressive strength increases, and not only critical compression and pressure loss can be prevented, but also adsorption when a ligand is immobilized is maintained, improved, preferably improved, and completed also the invention according to the second embodiment (improvement in carrier for ligand immobilization).

That is, the invention according to the second embodiment (improvement in carrier for ligand immobilization) is as follows.

(16) A carrier for ligand immobilization obtained by shrinking polysaccharide porous beads not less than 10% by a shrinkage rate defined by the following formula, and crosslinking the polysaccharide porous beads:

$$\text{Shrinkage rate (\%)} = (1 - V_2/V_1) \times 100$$

(wherein, $V_1$ indicates the gel volume of polysaccharide porous beads before shrinkage, and $V_2$ indicates the gel volume of polysaccharide porous beads after shrinkage).

(17) The carrier according to (16), wherein the carrier is produced through a shrinking step of bringing the polysaccharide porous beads into contact with a water-soluble organic solvent and alkali water.

(18) The carrier according to (17), wherein the carrier is produced by shrinking and crosslinking in the presence of a crosslinking agent in the shrinking step, or by conducting a crosslinking step of crosslinking obtained shrunk beads after the shrinking step.

(19) The carrier according to (18), wherein an additional crosslinking step of brining the beads obtained by the said crosslinking step into contact with a crosslinking agent and alkali water is conducted once or more.

(20) The carrier according to any one of (16) to (19), wherein the polysaccharides is cellulose or agarose

(21) The carrier according to any one of (17) to (20), wherein the water-soluble organic solvent is at least one selected from the group consisting of an alcohol solvent, a sulfoxide solvent, an amide solvent, a ketone solvent and an ether solvent.

(22) The carrier according to any one of (19) to (21), wherein an alcohol solvent is not used in the additional crosslinking step.

(23) An adsorbent obtained by immobilizing a ligand on the carrier according to any one of (16) to (22).

(24) The adsorbent according to (23), wherein the ligand is an affinity ligand.

(25) The adsorbent according to (24), wherein the affinity ligand is protein A, protein G, or protein L.

(26) A method for purifying an antibody by affinity chromatography, comprising the steps of: bringing a source material into contact with the adsorbent according to (24) or (25), to adsorb an antibody, and appropriately washing the antibody adsorbed on the adsorbent, and adding an eluent for liberating the antibody from the adsorbent, to collect the antibody from the eluate.

Specific examples recited in this description can be appropriately used in combination of one or more kinds unless otherwise noted.

Effects of the Invention

1. In the Case of the First Embodiment (Improvement in Porous Cellulose Beads)

According to the process of the first embodiment of the present invention, by changing the solution temperature, and the concentration of sodium hydroxide, it is possible to change the particle diameter and the internal structure of the cellulose beads, and it becomes possible to provide porous cellulose beads that can be used as an adsorbent for various substances.

2. In the Case of the Second Embodiment (Improvement in Carrier for Ligand Immobilization)

In the second embodiment of the present invention, since the polysaccharide porous beads are shrunk by a predetermined amount or more, while they are crosslinked, it is possible to improve the compressive strength. By immobilizing a ligand on the polysaccharide porous beads having improved compressive strength as a carrier, it is possible to maintain or improve, preferably improve not only the strength but also the adsorption.

BRIEF DESCRIPTION OF THE DRAWINGS

FIG. 1 is a SEM photograph of a cellulose bead of the present invention (first embodiment) obtained in Example 1 regarding the first embodiment.

FIG. 2 is a SEM photograph of cellulose obtained in Comparative Example 1 regarding the first embodiment.

FIG. 3 shows particle diameter distributions of cellulose beads obtained in Example 1 to Example 4 regarding the first embodiment.

FIG. 4 shows $K_{av}$ values of cellulose beads obtained in Example 1 to Example 4 regarding the first embodiment.

FIG. 5 is a chart regarding the second embodiment, and is a graph showing the relationship between the shrinkage rate in the shrinking and crosslinking step and the 20% compressive stress of the shrunk and cross-linked beads.

MODE FOR CARRYING OUT THE INVENTION

Hereinafter, the present invention will be described in the order of improvement in porous cellulose beads (first embodiment), and improvement in a carrier for ligand immobilization (second embodiment).

1. Improvement in Porous Cellulose Beads (First Embodiment)

(1) Cellulose Micro Dispersion

In process of the present invention (first embodiment), first, cellulose is mixed with an alkali aqueous solution to prepare a cellulose micro dispersion at low temperature. Retaining at low temperature contributes to producing excellent porous cellulose beads. In the micro dispersion preparing step, for example, cellulose is micro dispersed in an alkali aqueous solution of an alkali concentration of not more than 10 wt % and not less than 7.5 wt % (preferably not less than 8 wt %, particularly 9-8 wt %) at a temperature of about −5-10° C. (preferably 0° C.-4° C.). Alternatively, cellulose is mixed with an alkali aqueous solution so that the mixture (micro dispersion) has the alkali concentration and the temperature within the aforementioned ranges. Examples of the alkali aqueous solution include a sodium hydroxide aqueous solution and a potassium hydroxide aqueous solution.

The concentration of cellulose in the cellulose micro dispersion is, for example, not less than 5.5 wt %, and may be not less than 8 wt %. The upper limit of the concentration of cellulose is for example, not more than 20 wt %, preferably not more than 10 wt %.

As the cellulose, various celluloses can be used, and for example, any of regenerated cellulose, crystalline cellulose, microcrystalline cellulose, and cellulose acetate may be used.

The degree of polymerization of cellulose is for example, not more than 1000, preferably not more than 500, more preferably not more than 300. The lower limit of the degree of polymerization is, for example, not less than 10, preferably not less than 100, more preferably not less than 200.

The median particle diameter of the cellulose is, for example, not less than 10 μm, preferably not less than 20 μm, not less than 45 μm, and the upper limit thereof is, for example, not more than 500 μm, more preferably not more than 300 μm, further preferably not more than 200 μm.

(2) Cellulose Slurry

Preferably, after micro-dispersing cellulose in the alkali aqueous solution, water is added, and the slurry temperature is raised. This temperature raising step is not necessary, and the cellulose slurry may be prepared by adding water without changing the temperature. In any case, when the micro dispersion is made into a slurry by addition of water, excellent porous cellulose beads are produced.

The alkali concentration of the cellulose slurry is, for example, not less than 3 wt %, preferably not less than 5 wt % and not more than 9 wt %, more preferably not less than 5 wt % and not more than 8 wt % (particularly not more than 7 wt %). In the present invention, although the bead particle diameter can be made smaller by decreasing the alkali concentration, cellulose is no longer micro-dispersed when the alkali concentration is not more than 5 wt % (particularly less than 3 wt %).

The concentration of cellulose in the cellulose slurry is, for example, not less than 1 wt %, preferably not less than 2 wt %, and the upper limit thereof is, for example, not more than 7 wt %, preferably not more than 5.4 wt %.

In the cellulose slurry, the mass ratio between the amount of water existing in the micro dispersion (initial water amount), and the amount of adding water (water adding amount) is, for example, 95:5-30:70, preferably 90:10-40:60.

The higher the temperature of the cellulose slurry, the smaller the particle diameter of beads can be made, and the higher the temperature, the larger the pore size of beads can be made. As a specific temperature range, the temperature of the cellulose slurry is preferably not less than 4° C. and not more than 25° C., further preferably not less than 4° C. and not more than 20° C. When the temperature of the cellulose slurry is not less than the upper limit, cellulose is no longer micro-dispersed.

When the micro dispersion is made into a slurry by raising the temperature, the difference in temperature between the slurry and the micro dispersion is, for example, not less than 1° C., preferably not less than 5° C., more preferably not less than 10° C., and the upper limit thereof is, for example, not more than 30° C., preferably not more than 25° C., more preferably not more than 20° C.

(3) Droplet Preparing Step

Then, the cellulose slurry obtained in the manner as described above can be brought into contact with a coagulation liquid to make porous cellulose beads, and as is necessary, the cellulose slurry may be prepared into droplet in which droplet (water phase) containing cellulose are dispersed in other liquid (oil phase) before it is brought into contact with the coagulation liquid. By coagulating cellulose after formation of droplet, characteristics of porous cellulose beads are further improved. In the droplet preparing step, for forming cellulose porous beads, a cellulose slurry is dispersed in a water-insoluble liquid, and cellulose droplet are formed in the water-insoluble liquid.

As the water-insoluble liquid, halogenated hydrocarbons such as dichlorobenzene, aliphatic hydrocarbons such as hexane, esters (particularly acetic esters) such as ethyl acetate, straight-chain saturated fatty acid having 6 to 12 carbons, unsaturated fatty acid having 16 to 24 carbons, animal fats and vegetable oils having a melting point of not more than 100° C., hydrogenated animal fats and vegetable oils, fractionated oil prepared by fractionating and purifying a high-melting point fraction of animal fats and vegetable oils or hydrogenated animal fats and vegetable oils, unsaturated fatty acid triglycerides, edible waxes, fats and oils from microalgae, fats and oils from microorganisms, medium-chain fatty acid triglycerides, and unsaturated fatty acid triglycerides can be recited. These water-insoluble liquids can be used singly or in combination of two or more kinds. Preferred water-insoluble liquids include halogenated hydrocarbons, aliphatic hydrocarbons, esters, and particularly halogenated hydrocarbons.

The amount of water-insoluble liquid is not particularly limited as long as it can disperse the droplet phase of the cellulose slurry, and it is, for example, not less than 50 parts by mass, preferably not less than 100 parts by mass, more preferably not less than 200 parts by mass, relative to 100 parts by mass of the cellulose slurry, and the upper limit thereof is, for example, not more than 5000 parts by mass, preferably not more than 2000 parts by mass, more preferably not more than 1000 parts by mass.

In preparing the droplet, a surfactant may be used as is necessary. By using a surfactant, it is possible to form the droplet phase of the cellulose slurry stably. As the surfactant, nonionic surfactants are preferred, and specific examples include sorbitan fatty acid esters such as sorbitan laurate, sorbitan stearate, sorbitan oleate, and sorbitan trioleate. These surfactants may be used singly or in combination of two or more kinds. The amount of the surfactant is not particularly limited, and is for example, not less than 10 parts by mass, preferably not less than 30 parts by mass, more preferably not less than 50 parts by mass, relative to 100 parts by mass of cellulose, and the upper limit thereof is, for example, not more than 1000 parts by mass, preferably not more than 300 parts by mass, more preferably not more than 200 parts by mass.

The surfactant may be, for example, added to a water-insoluble liquid to make a mixture, and then the mixture may be brought into contact with the cellulose slurry.

While the method for dispersing the cellulose slurry is not particularly limited, the cellulose droplet can be uniformly dispersed in a water-insoluble liquid, for example, by stirring with a stirring blade or by stirring with a homogenizer. Also a static mixer can be used. When the stirring intensity is increased at this time, the size of the cellulose droplet decreases, and thus the particle diameter of the obtainable cellulose beads decreases.

The temperature during preparation of droplet can be set, for example, within the same range as the temperature range of the cellulose slurry. As long as this temperature range is maintained, the temperature may be lowered or raised during preparation of droplet from the cellulose slurry, and the temperature difference between during production of the cellulose slurry and during production of droplet (temperature during preparation of droplet—temperature of the cellulose slurry) is typically not less than −5° C., preferably not less than −3° C., more preferably not less than −1° C., and the upper limit thereof is, for example, not more than 5° C., preferably not more than 3° C., more preferably not more than 1° C., and most preferably the temperature difference is 0° C.

For adjusting the temperature during preparation of droplet within the aforementioned range, it is desired to preliminarily adjust the temperature of the water-insoluble liquid (a surfactant may be contained as is necessary) before mixing with the cellulose slurry. In this case, the temperature difference between the cellulose slurry and the water-insoluble liquid (temperature of water-insoluble liquid—temperature of cellulose slurry) is typically not less than −5° C., preferably not less than −3° C., more preferably not less than −1° C., and the upper limit thereof is, for example, not more than 5° C., preferably not more than 3° C., more preferably not more than 1° C., and most preferably the temperature difference is 0° C.

(4) Coagulating Step

The cellulose slurry or the cellulose droplet dispersion formed in this manner is brought into contact with a liquid that can mingle with the cellulose slurry but shows cellulose coagulability, namely a coagulation solvent. During mixing the dispersion and the cellulose coagulable liquid, cellulose droplet and the cellulose coagulable liquid come into contact with each other, and cellulose beads are formed. Thereafter, the formed cellulose beads are collected.

It is recommended that mixing of the cellulose slurry or droplet dispersion with the coagulation solvent is conducted under a stirred conduction similar to that during preparation of the droplet. The temperature during this mixing (coagulation) is preferably comparable to the temperature of the cellulose slurry or its droplet dispersion, and is for example, within ±10° C., preferably within ±5° C., more preferably within ±2° C., relative to the temperature of the cellulose slurry or its droplet dispersion.

As the coagulation solvent, for example, alcohols, glycols and the like can be used. Examples of the alcohols include isobutanol, 2-butanol, sec-butanol, 2-methyl-2-propanol (i.e., tert-butanol), 1-prop anol, 2-prop anol, ethanol, and methanol, and these may be used singly or in combination of two or more kinds.

Examples of the glycols include glycerol, ethylene glycol, and propylene glycol, and these may be used singly or in combination of two or more kinds.

(5) Isolating Step

The cellulose beads obtained by the first embodiment of the invention are porous beads, and the size of the pore, and the particle diameter can be controlled by changing the temperature of cellulose slurry, and the alkali concentration as described above.

The obtained porous beads can be isolated from the coagulation liquid by solid-liquid separation by an appropriate method such as filtration, centrifugation or the like, and drying as necessary. In this isolating operation, porous cellulose beads may be washed with an appropriate solvent (such as water, a water-soluble solvent such as alcohol).

The median particle diameter of the porous beads obtained in this manner is, for example, not less than 50 μm, preferably not less than 70 and the upper limit thereof is, for example, not more than 100 μm, not more than 95 μm.

The exclusion limit molecular weight of the porous cellulose beads is, for example, not less than $1.0 \times 10^6$, preferably not less than $2.3 \times 10^6$, more preferably not less than $1.0 \times 10^7$, and the upper limit is, for example, not more than $1.0 \times 10^{11}$, preferably not more than $8.0 \times 10^{10}$.

(6) Other Respects

The porous cellulose beads obtained in the manner as described above can be used as an adsorbent for various substances. They can be used also as a carrier for immobilizing a ligand. When they are used as a carrier, it is preferred that the porous cellulose beads are crosslinked. As a method for crosslinking the porous cellulose beads, the invention according to the second embodiment (crosslinking after shrinkage, or crosslinking while shrinking, etc.) as will be described later may be conducted as it is, or a known crosslinking method may be conducted.

When a known crosslinking method is conducted, halohydrins such as epichlorohydrin, epibromohydrin, and dichlorohydrin; bifunctional bisepoxides (bisoxirane); and multifunctional polyepoxides such as glycerol polyglycidyl ether (polyoxirane) can be recited as a crosslinking agent. Among others, the method shown in JP-A-2008-279366 can be used particularly preferably. This publication is incorporated by reference in the present application.

The porous cellulose beads may be classified before crosslinking or after crosslinking. The lower limit of particle diameter of porous cellulose beads after classification is, for example, 10 μm, preferably 20 μm, more preferably 30 μm, and the upper limit is, for example, 200 μm, preferably 150 μm, more preferably 125 μm.

Further, to the crosslinked carrier, a ligand may be immobilized appropriately. The kind of the ligand and the immobilizing method can be appropriately selected from known scopes, and they may be conducted in a similar manner as in the later-described second embodiment.

2. Improvement in Carrier for Ligand Immobilization (Second Embodiment)

Next, improvement in a carrier for ligand immobilization (second embodiment) will be described.

(1) Polysaccharide Porous Beads

The carrier for ligand immobilization of the invention of the second embodiment is crosslinked beads obtained by crosslinking polysaccharide porous beads. Polysaccharides used for polysaccharide porous beads include agarose, cellulose, dextrin, chitosan, chitin, and derivatives thereof. Preferred polysaccharides include cellulose and agarose, with cellulose being particularly preferred.

The polysaccharide porous beads before crosslinking may be a commercially available product, or may be obtained by a known process using polysaccharides. For example, the cellulose porous beads can be obtained by a process including granulation and coagulation after dissolving or dispersing cellulose in an appropriate solution (for example, JP-W-2009-242770, WO2996/025371, U.S. Pat. Nos. 4,634,470, 5,410,034, WO2012/121258). Of course, the porous cellulose beads before crosslinking obtained by the first embodiment of the invention may be used.

The lower limit of the exclusion limit molecular weight of polysaccharide porous beads is, for example, $1.0 \times 10^5$, preferably $5.0 \times 10^5$, more preferably $1.0 \times 10^6$, and the upper limit is, for example, $1.0 \times 10^{12}$, preferably $5.0 \times 10^{11}$, more preferably $1.0 \times 10^{11}$. By using the polysaccharide porous beads having large exclusion limit molecular weight as described above, it is possible to obtain an adsorbent suited for separation of substances having large molecular weight like antibodies.

The exclusion limit molecular weight can be determined in the following manner. Specifically, polysaccharide porous beads are packed in a column (packed beads capacity is defined as $V_t$), and a solution containing blue dextran 200, and various molecular weight markers is caused to run through the column. A liquid amount ($V_0$) required for the first peak to be detected after starting running of blue dextran 200, and a liquid amount ($V_R$) required for the first peak to be detected after running of each marker are determined, and a gel phase distribution coefficient ($K_{av}$) of each marker is determined according to the following formula (1). On a graph in which distribution coefficient ($K_{av}$) is assigned to the vertical axis, and a natural logarithm of molecular weight is assigned to the horizontal axis, the measurement result in each marker is plotted, and the following formula (2) is determined based on the part showing linearity (in the formula, k and b are constants). In the formula (2), the molecular weight at which the distribution coefficient ($K_{av}$) is 0 is defined as exclusion limit molecular weight.

$$K_{av}=(V_R-V_0)/(V_t-V_0) \quad (1)$$

$$K_{av}=k \times \text{Ln(molecular weight)}+b \quad (2)$$

(2) Shrinking Step

The second embodiment (improvement in carrier for ligand immobilization) of the present invention is featured in that polysaccharide porous beads are shrunk. By utilizing shrinkage, it is possible to suitably increase the compressive strength.

The degree of shrinkage can be evaluated based on the shrinkage rate determined by the following formula.

$$\text{Shrinkage rate (\%)}=(1-V_2/V_1) \times 100$$

(wherein, $V_1$ indicates the gel volume of polysaccharide porous beads before shrinkage, and $V_2$ indicates the gel volume of polysaccharide porous beads after shrinkage. In the present invention, as being described later, there is a case that beads are shrunk in the presence of a crosslinking agent. In such a case, the $V_1$ indicates the gel volume of polysaccharide porous beads before shrinking and crosslinking, and $V_2$ indicates the gel volume of polysaccharide porous beads after shrinking and crosslinking.)

In the present invention, the lower limit of the shrinkage rate is 10%, preferably 15%, more preferably 20%, and the upper limit is 60%, preferably 50%. The larger the shrinkage rate, the higher the compressive strength (compressive stress) of the carrier can be made.

The gel volume means the volume of the sedimentation part when the beads sediment. Specifically, it is determined by using a sample slurry prepared by washing a beads-containing solution (reaction solution) before or after shrinkage, and replacing with RO water (Reverse Osmosis water). The concentration of the sample slurry is roughly such that the gel volume concentration (gel volume/sample slurry volume) of the sample slurry is 30-70% by volume, and a 50 mL centrifugal tube containing the sample slurry is fixed on a small vibrator (VIBRATORY PACKER, VP-4D available from SINFONIA TECHNOLOGY, or an equivalent article) at 25° C., and the volume of the beads part is read from the scale of the centrifugal tube after vibration is conducted until sedimentation of beads stops, and thus the gel volume in the sample slurry can be determined. Each of gel volumes $V_1$, $V_2$ in the above formula indicates the gel volume of the total amount of beads used in the shrinking step, and when the sample slurry is prepared by sampling part of the reaction solution, the gel volumes $V_1$, $V_9$ of the total amount of beads are determined from the gel volume of the sample slurry and the sampled proportion.

For shrinking the polysaccharide porous beads by a predetermined amount or larger, it is recommended to bring the polysaccharide porous beads into contact with a water-soluble organic solvent, alkali and water. By contacting with alkali, shrinkage starts. Here, presence of the water-soluble organic solvent results in significant increase in the shrinkage rate compared with the case where the water-soluble organic solvent is absent.

Examples of the water-soluble organic solvent used in the second embodiment include alcohol solvents such as methanol, ethanol, and propanol; sulfoxide solvents such as dimethyl sulfoxide; amide solvents such as dimethyl formamide, dimethyl acetamide, and N-methylpyrrolidone; ketone solvents such as acetone; ether solvents such as dioxane and tetrahydrofuran; and glycol solvents such as ethylene glycol and diethylene glycol.

Preferred water-soluble organic solvents include alcohol solvents, sulfoxide solvents, amide solvents, ketone solvents, and ether solvents, and more preferred water-soluble organic solvents include methanol, ethanol, dimethyl sulfoxide, dimethyl formamide, dimethyl acetamide, acetone, and dioxane, and most preferred water-soluble organic solvents include ethanol and dimethyl sulfoxide. These may be used as two or more kinds of mixed solvent.

As alkali used for alkali water, an alkali metal-containing compound is preferred, and for example, alkali metal hydroxide such as lithium hydroxide, sodium hydroxide, and potassium hydroxide can be used. These alkalis may be used singly or in combination as appropriate. Preferred alkali is sodium hydroxide. While the alkali water is preferably aqueous solution, it may be dispersion. It is usual to preliminarily prepare alkali water, and add the alkali water to the reaction solution; however, the alkali water may be prepared in the reaction solution as is necessary.

(3) Crosslinking

The present invention is also featured in that shrinking of the polysaccharide porous beads is combined with crosslinking. By immobilizing a ligand on the polysaccharide porous beads having improved strength owing to improvement in the compressive strength by shrinkage and the compressive strength by crosslinking, as a carrier, it is possible to maintain and improve the adsorption.

Specifically, in the shrinking step, it is preferred to cause shrinking and crosslinking in the presence of a crosslinking agent (it is preferred that the shrinking step is a shrinking and crosslinking step that also serves as a crosslinking step); however, the obtained shrunk beads after the shrinking step may be crosslinked by a known crosslinking method. Also in crosslinking after the shrinking step, a crosslinking agent can be used. In any case, it is recommended that the degree of crosslinking of the polysaccharide porous beads for use in the shrinking step is low (particularly, they are not crosslinked at all). As the degree of crosslinking of the polysaccharide porous beads before the shrinking step increases, shrinkage of the polysaccharide porous beads at the shrinking step becomes more difficult, and a desired shrinkage rate is difficult to be achieved.

As the crosslinking agent, halohydrins such as dichlorohydrin, or epoxy compounds can be preferably used, and examples of the epoxy compounds include monoepoxy compounds such as epichlorohydrin and epibromohydrin; diepoxy compounds such as bisoxirane and diglycidyl ethers; and polyepoxy compounds such as polyoxirane and polyglycidyl ethers.

(4) Shrinking Simplex Step, Shrinking and Crosslinking Step

When the shrinking step does not serve also as a crosslinking step (referred to as a shrinking simplex step), the step can be conducted by bringing the polysaccharide porous beads into contact with the water-soluble organic solvent, alkali and water as described above. When the shrinking step serves also as a crosslinking step (shrinking and crosslinking step), the step can be conducted by bringing the polysaccharide porous beads into contact with the water-soluble organic solvent, the crosslinking agent, and the alkali water. The procedure, amounts, temperature and the like in bringing these polysaccharide porous beads, water-soluble organic solvent, alkali water, and the crosslinking agent as necessary into contact with each other can be appropriately set. In the shrinking and crosslinking step, preferably, a dispersion is prepared from the polysaccharide porous beads, the crosslinking agent, and the water-soluble organic solvent, and the alkali aqueous solution is added to the dispersion. After allowing to react for a predetermined time after adding the alkali aqueous solution, the alkali aqueous solution may be re-added once or more times. When the alkali aqueous solution is re-added, the crosslinking reaction before re-addition is also referred to as a main shrinking and crosslinking reaction.

The lower limit of the slurry concentration (concentration of polysaccharide porous beads) in the reaction solution in the shrinking simplex step, and the slurry concentration (concentration of polysaccharide porous beads) in the main shrinking and crosslinking reaction (reaction before re-adding the alkali aqueous solution) solution in the shrinking and crosslinking step is, for example, 10% by volume, preferably 20% by volume, more preferably 25% by volume, and the upper limit is, for example, 70% by volume, preferably 60% by volume, more preferably 50% by volume. The slurry concentration means gel volume/total liquid amount (volume).

The lower limit of the rate of the water-soluble organic solvent in the reaction solution in the shrinking simplex step, and the rate of the water-soluble organic solvent in the main shrinking and crosslinking reaction (the reaction before re-adding the alkali aqueous solution) solution in the shrinking and crosslinking step is, for example, 0.30, preferably 0.40, more preferably 0.50, and the upper limit is, for example, 0.90, preferably 0.80, more preferably 0.65. The rate of the water-soluble organic solvent means organic solvent volume/(organic solvent volume+alkali water volume), and the organic solvent volume includes the volume of the organic solvent used for gelation of the polysaccharide porous beads. For example, when the water of aqueous gel of the polysaccharide porous beads is replaced with the organic solvent, the volume of the beads after replacement with the organic solvent is generally equivalent to the volume of the organic solvent.

The lower limit of the concentration of the crosslinking agent in the main shrinking and crosslinking reaction solution (volume of crosslinking agent/total liquid amount of reaction solution (volume)) is, for example, 5% by volume, preferably 10% by volume, and the upper limit is, for example, 50% by volume, preferably 40% by volume, more preferably 30% by volume.

The lower limit of each of the alkali concentration in the reaction solution in the shrinking simplex step, and the alkali concentration in the main shrinking and crosslinking reaction solution in the shrinking and crosslinking step is, for example, 0.1 M, preferably 0.3 M, more preferably 0.5 M, and the upper limit is, for example, 2.0 M, preferably 1.5 M, more preferably 1.2 M. In calculating the alkali concentration, the volume of the denominator indicates a sum of the organic solvent volume and the alkali water volume.

The lower limit of the temperature in causing both crosslinking and shrinking of the polysaccharide porous beads to proceed by adding the alkali water in the shrinking and crosslinking step is, for example, 0° C., preferably 20° C., more preferably 30° C., and the upper limit is, for example, 80° C., preferably 70° C., more preferably 50° C. Also in the shrinking simplex step, the temperature ranges are applicable (5) Additional Crosslinking Step In the present invention, after crosslinking polysaccharide porous beads by crosslinking at the time of shrinking reaction (shrinking and crosslinking step) or by crosslinking after the shrinking reaction, an additional crosslinking step for further crosslinking the obtained crosslinked beads may be conducted. The additional crosslinking step may be conducted once or repeated several times. By conducting the additional crosslinking step once or more, the compressive strength of the crosslinked beads can be further improved.

In the additional crosslinking step, there is a case that a shrinking phenomenon little occurs even if the water-soluble organic solvent is used. The additional crosslinking step can be conducted in the same manner as in the shrinking and crosslinking step described above except that use of the water-soluble organic solvent is optional. Therefore, the specific examples of the crosslinking agent, and alkali water to be used, the procedure, and use amounts are also similar. The use amount of the water-soluble organic solvent in the aforementioned shrinking and crosslinking step is applied while it is read as a preferred range in the additional crosslinking step.

In the additional crosslinking step, it is preferred that an alcohol solvent is not used. The preferred modes include the mode not using a protonic organic solvent, and the mode not using a water-soluble organic solvent, and also include the mode using an aprotic water-soluble organic solvent as a water-soluble organic solvent. When the alcohol solvent is not used, the crosslinking reaction is easy to proceed and the strength can be further improved in comparison with the case where the alcohol solvent is used. As the aprotic water-soluble organic solvent, aprotic solvents among the aforementioned water-soluble organic solvents can be used singly or in combination.

(6) Preliminary Crosslinking Step

Further, in the present invention, prior to the shrinking step (including the shrinking and crosslinking step), a preliminary crosslinking step for preliminarily crosslinking polysaccharide porous beads may be conducted. The preliminary crosslinking step can be conducted by a similar operation as in the additional crosslinking step except that the degree of cross linking (crosslinking agent concentration or the like) is small. In the present invention, it is preferred to conduct the shrinking step (including the shrinking and crosslinking step) without conducting the preliminary crosslinking step.

In the preliminary crosslinking step, the shrinking and crosslinking step, crosslinking after the shrinking step, and the additional crosslinking step, a reaction promoter, a reducing agent such as sodium borohydride or an inorganic salt may be used as necessary. By using the inorganic salt, it is possible to further increase the compressive stress of the crosslinked beads. Examples of the inorganic salt include hydrochlorides, sulfates, phosphates and borates of alkali metal or alkali earth metal, and sodium sulfate is particularly preferred. These inorganic salts may be used singly or in combination of two or more kinds. After end of crosslinking, a curing treatment may be conducted as is necessary. In the curing treatment, for example, a pressurizing and heating treatment using an autoclave is convenient.

(7) Crosslinked Beads (Carrier for Ligand Immobilization)

The crosslinked beads obtained in the manner as described above can be used as a carrier for ligand immobilization. The lower limit of the 20% compressive stress of the crosslinked beads is, for example, 0.06 MPa, preferably 0.072 MPa, more preferably 0.092 MPa, and the upper limit is, for example, 0.28 MPa, preferably 0.20 MPa. The 20% compressive stress means the stress required for compressing by 20% after causing the beads-containing slurry to sediment on the filter having a pore diameter of 5.00 μm to such a degree that they no longer sediment even under vibration.

The crosslinked beads are desired to have higher linear velocity at which critical compression occurs. In the crosslinked beads of the present invention, the linear velocity of critical compression is, for example, not less than 700 cm/h, preferably not less than 1000 cm/h, more preferably not less than 1500 cm/h. The linear velocity of critical compression means the linear velocity when water is run through a column packed with the crosslinked beads, and the inlet pressure continues to rise to finally disable the liquid running.

The crosslinked beads may be classified as necessary by a screen or the like. The lower limit of particle diameter of the crosslinked beads after classification is, for example, 10 μm, preferably 20 μm, more preferably 30 μm, and the upper limit is, for example, 200 μm, preferably 150 μm, more preferably 125 μm.

(8) Ligand

By immobilizing a ligand on the crosslinked beads serving as a carrier, an adsorbent can be obtained. The crosslinked beads carrier of the present invention can maintain and improve the adsorption by the ligand for its strength.

As the ligand, those having affinity with the object to be adsorbed can be appropriately used, and examples of such a ligand include an affinity ligand, a charged group, and a hydrophobic group, and these may be introduced singly or may be introduced while a plurality of these are combined appropriately. These ligands can be introduced by a known method, and the obtained adsorbent can be suitably used as a column packing material for various chromatography such as affinity chromatography, ion exchange chromatography, chelate chromatography, and hydrophobic interaction chromatography. Further, the crosslinked beads carrier of the present invention is suited for separation and purification of an antibody as an objective substance because of its pore size, and the absorbent into which an affinity ligand, a charged group, a hydrophobic group or the like can be suitably used for purification of an antibody.

A preferred ligand in the present invention is an affinity ligand. While the affinity ligand is not particularly limited as long as it has a feature of capable of specifically binding with an antibody or the like as a target molecule, it is preferably a peptidic, proteinic or synthetic compound. From the view point of specificity to a target molecule, a peptidic or proteinic ligand is further preferred, and among others, particularly preferred antibody affinity ligands include protein A, protein G, protein L, protein H, protein D, protein Arp, protein FcγR, antibody-binding synthetic peptide ligands and their relative substances. Protein used as a ligand in the present description encompasses variants thereof. Natural products, genetically engineered products and the like can be used without any restriction, and various variants that are generally produced can be used. Also those containing an antibody-binding domain and its variant, fusion proteins and so on can also be used. For example, for improving the bindability with the antibody, those having a sequence modified so that the antibody binding protein is site-specifically immobilized to the substrate material (for example, protein with controlled position and number of lysine residues as described in JP 4179517 B1 and JP-A-2008-214350) can also be used.

Also usable is protein that is produced from a bacterial extract or a culture supernatant by combination and/or repetition of purifying techniques selected from the techniques such as molecular weight fractionation, fractionating precipitation method using various chromatography including ion exchange chromatography, hydrophobic interaction chromatography, gel filtration chromatography and hydroxyapatite chromatograph, and membrane separation technique. Preferred affinity ligands are protein A, protein G, protein L and variants thereof, and protein A is particularly preferred. Protein A attracts attentions as a ligand capable of specifically adsorbing and eluting immunoglobulin (IgG) or the like. An adsorbent on which protein A is immobilized attracts attentions as a therapeutic adsorbent for rheumatism, hemophilia, and dilated cardiomyopathy. Also in the field of antibody drug purification, an adsorbent capable of conducting purification of antibodies such as IgG in large scale, at high speed, at low cost is demanded.

Generally, protein A indicates one kind of cell wall protein produced by a gram positive bacterium, *Staphylococcus aureus*, and consists of a signal sequence S, five IgG binding domains (E domain, D domain, A domain, B domain, C domain), and a XM region which is a cell wall binding domain (attributed to Hober S. et al., "J. Chromatogr. B", 2007, vol. 848, pp. 40-47). As protein A for use as a ligand for IgG affinity purification, protein consisting exclusively of five IgG binding domains (SEQ ID NO: 1) is generally used. Protein A used herein also includes proteins having either one or more domains selected from E, D, A, B, and C domains, as well as the general protein A and protein consisting exclusively of E, D, A, B, and C domains, and it may be protein consisting exclusively of the one having, for example, a plurality of (e.g., three to eight, particularly five) C domains in series.

Preferred examples of protein A include protein A having alkali resistance and orientation-controlled protein A. Since the carrier of the present invention has strengthened alkali resistance by the effect of crosslinking or the like, by strengthening the alkali resistance of the ligand, it is possible to increase the alkali resistance as an adsorbent. Examples of protein A having alkali resistance include protein in which an alkali sensitive residue (either one of asparagine residue, glutamine residue and so on) in the protein A is deleted, or protein in which the alkali sensitive residue is replaced with an alkali resistant residue (for example, natural amino acid residues other than an asparagine residue and a glutamine residue, preferably, natural amino acid residues further excluding a cysteine residue, more preferably a lysine residue, an asp artic acid residue, a leucine residue and so on) (for example, JP-W-2002-527107); protein having a domain (Z domain) in which the glycine residue at position 29 in B domain of protein A is replaced with an alanine residue (for example, JP-B-8-11069); protein in which the glycine residue at position 29 in C domain of protein A is replaced with a natural amino acid residue other than a glycine residue (for example, alanine residue, leucine residue, isoleucine residue, phenylalanine residue, tyrosine residue, tryptophan residue, glutamine residue, arginine residue, or methionine residue), and protein in which a plurality of (particularly five) C domains in which the residue at position 29 is replaced are exclusively connected (for example, WO2010/110288).

Examples of orientation-controlled protein A include protein in which a cysteine residue is granted (replaced, added, or the like) in the C terminal or the N terminal of protein A (for example, JP-A-2008-101023); (A) protein in which not less than ½, preferably not less than ⅔, more preferably not less than ¾, particularly preferably all of the lysine residues in protein A are replaced with other amino acid residue, (B) preferably, protein wherein other amino acid is arginine, glutamine, asparagine, aspartic acid, glutamic acid, isoleucine, histidine or glycine in protein of (A), (C) more preferably, protein wherein one or more lysine residues are granted (replaced, added or the like) in a terminal (particularly C terminal) in protein of (A) or (B) (for example, WO2012/133349). Also orientation-controlled protein A having alkali resistance by combining these modifications may be used.

The lower limit of the introducing amount of the affinity ligand is, for example, 2 mg, preferably 4 mg, more preferably 10 mg per 1 mL of crosslinked beads, and the upper limit is, for example, 40 mg, preferably 30 mg, more preferably 20 mg per 1 mL of crosslinked beads.

The introducing amount of the affinity ligand can be determined by a known method.

For immobilizing the affinity ligand on the crosslinked beads, various known immobilizing methods, e.g., a cyanogen bromide method, a trichlorotriazine method, an epoxy method, and a tresyl chloride method can be appropriately employed. For the reasons of safety, easiness of immobilizing reaction, and ability to immobilizing produced protein or peptide with a relatively easy method, a method of introducing a formyl group into crosslinked beads, and reacting the formyl group and an amino acid of the affinity ligand (for example, WO2010/064437) is preferred treatment.

Formyl groups can be introduced into the crosslinked beads by cutting C—C bonds in a, 6-diol units contained in polysaccharides. When an epoxy compound such as epichlorohydrin is used as the crosslinking agent, formyl groups can also be introduced by oxidizing and cleaving diols obtained by hydrolysis of epoxy groups. Regarding the amount of the formyl groups, the lower limit is, for example, 1 μmol, preferably 5 μmol, more preferably 10 lima particularly preferably 20 μmol, most preferably 30 μmol per 1 mL of crosslinked beads, and the upper limit is, for example, 500 μmol, preferably 250 μmol, more preferably 125 μmol, particularly preferably 60 μmol, most preferably 50 μmol, Active groups remaining after introduction of the affinity ligand are subjected to an inactivating According to the present invention, since the strength of the carrier is strengthened by compression, the adsorptive performance of the adsorbent in which the affinity ligand is immobilized is also maintained and improved. When protein A is used as the affinity ligand, the adsorptive characteristic of the adsorbent can be evaluated, for example, by 5% dynamic binding capacity (DBC) of human immunoglobulin (IgG). When the adsorption treatment is conducted for a residence time (RT) of 3 minutes, the lower limit of 5% DBC is, for example, 20 mg, preferably 30 mg, more preferably 40 mg, per 1 mL of adsorbent, and the upper limit is, for example, 100 mg, preferably 60 mg.

The 5% DBC can be determined by allowing a phosphate buffer at pH 7.4 to run through the column packed with the adsorbent, and then allowing an IgG aqueous solution having a concentration of 1 mg/mL to run through the column.

The adsorbent can be used for purifying various target substances. The adsorbent may be used while it is packed in a column as is necessary. In one embodiment, the adsorbent is packed in a chromatography column. The column can be used for affinity chromatography by using a conventional liquid chromatography device or the like.

Also, the present invention provides a method for purifying antibodies from a mixture (source material). This method can include the step of contacting (loading) a mixture (source material) containing antibodies in the condition that antibodies selectively bind with the adsorbent obtained in the present invention, and optionally the step of eluting antibodies from the adsorbent by applying (allowing to run through) an eluent (preferably elution buffer) prepared by changing at least one condition (pH, salt strength). The antibodies can be collected from this eluate.

As the elution buffer, more specifically, a salt having different pH from the pH at the time of bringing into contact with the mixture containing antibodies (loading solution), or a salt of higher concentration can be used. This method can optionally include one or more washing steps. The washing step can be conducted, for example, after antibodies have bound the adsorbent, and before the antibodies are eluted from the adsorbent. Adsorption and elution of antibodies according to the present invention can be easily conducted in standard conditions as recommended for conventional commercially available products, and for example, the website of GE healthcare can be referred, for example.

The purification method described above can be combined with other chromatography to further improve the purification purity of antibodies.

The present application claims the benefit of priority based on the benefits of priority based on Japanese patent application No. 2013-202007 filed on Sep. 27, 2013 and Japanese patent application No. 2013-211453 filed on Oct. 8, 2013. The entirety of each of descriptions of Japanese patent application No. 2013-202007 filed on Sep. 27, 2013 and Japanese patent application No. 2013-211453 filed on Oct. 8, 2013 is incorporated herein by reference.

EXAMPLES

Hereinafter, the present invention is described more specifically by way of examples; however, it should be noted that the present invention is not limited by the following examples, and the present invention can be practiced with appropriate modification within the scope mentioned above or below, and any of such modification is included in the technical scope of the present invention.

1. Improvement in Porous Cellulose Beads (First Embodiment)

Example 1

8.65 g of powdery cellulose (pharmacopoeia cellulose PH-F20JP available from Asahi Kasei Chemicals Corporation) was dispersed in 112 g of water, and retained at 4° C. Then, 35 g of 34.5 wt % sodium hydroxide (available from NACALAI TESQUE, INC.) aqueous solution was added and stirred to obtain a cellulose micro dispersion. After stirring for 20 minutes, 16 g of water was added so that the concentration of sodium hydroxide was 7.0 wt %, and the concentration of cellulose was 5.0 wt %, and the temperature was raised to 15° C., and thus a cellulose slurry was obtained. In 890 g of 1,2-dichlorobenzene at 15° C. containing 9.2 g of sorbitan monooleate, the obtained cellulose slurry was dispersed to form a cellulose droplet dispersion. The cellulose droplet dispersion was put into a cylindrical container having an inner diameter of 85 mm. A two-stage turbine blade having a blade diameter of 45 mm was used for stirring, and the interval of blades was set at 75 mm. The dispersion was stirred at 600 rpm for 10 minutes, and 150 mL of methanol was added to obtain cellulose in the form of beads. The temperature at the time of forming the beads was equivalent to the temperature at the time of forming the cellulose droplet dispersion. Regarding the particle diameter of the obtained beads, a median particle diameter determined by using a laser diffraction/scattering particle diameter distribution measuring device (LA-950 available from HORIBA, Ltd.) was 90.2 μm. The obtained cellulose beads were washed with methanol, and then washed with water. Part of the collected cellulose beads were replaced with 2-methyl-2-propanol, and freeze-dried, and then analyzed by a scanning electron microscope (S-800 available from Hitachi, Ltd., hereinafter referred to as SEM). As a result, it was confirmed that the cellulose beads were porous beads as shown in FIG. 1.

The residual cellulose beads was classified by using a mesh with an opening of sieve of 38 μm and a mesh with an opening of sieve of 90 μm to collect beads within the range of 38 μm to 90 μm. The crosslinking reaction was conducted in the later-described method. Gel distribution coefficient ($K_{av}$) of the obtained crosslinked cellulose beads was calculated by conducting column packing and measurement in the later-described method. $K_{av}$ value for the marker molecular weight of 12400 was 0.723, $K_{av}$ value for the marker molecular weight of 67000 was 0.646, $K_{av}$ value for the marker molecular weight of 115000 was 0.595, and $K_{av}$ value for the marker molecular weight of 440000 was 0.525. The exclusion limit molecular weight calculated from these $K_{av}$ values was $6.0 \times 10^{10}$.

Example 2

Porous cellulose beads were obtained in the same manner and conditions as in Example 1 except that the temperature of cellulose slurry was raised to 10° C. and the temperature of 1,2-dichlorobenzene was 10° C. As a result, a particle median diameter of the obtained beads was 91.4 μm. A crosslinking reaction was conducted in the same manner as in Example 1, and $K_{av}$ was calculated. $K_{av}$ value for the marker molecular weight of 12400 was 0.562, $K_{av}$ value for the marker molecular weight of 67000 was 0.429, $K_{av}$ value for the marker molecular weight of 115000 was 0.377, $K_{av}$ value for the marker molecular weight of 440000 was 0.307, and $K_{av}$ value for the marker molecular weight of 660000 was 0.261. The exclusion limit molecular weight calculated from these $K_{av}$ values was $2.4 \times 10^7$.

Example 3

Porous cellulose beads were obtained in the same manner and conditions as in Example 1 except that the temperature of cellulose slurry was raised to 20° C. and the temperature of 1,2-dichlorobenzene was 20° C. As a result, a particle median diameter of the obtained beads was 80.3 µm. A crosslinking reaction was conducted in the same manner as in Example 1, and $K_{av}$ was calculated. $K_{av}$ value for the marker molecular weight of 12400 was 0.645, $K_{av}$ value for the marker molecular weight of 67000 was 0.528, $K_{av}$ value for the marker molecular weight of 115000 was 0.487, $K_{av}$ value for the marker molecular weight of 440000 was 0.400, and $K_{av}$ value for the marker molecular weight of 660000 was 0.374. The exclusion limit molecular weight calculated from these $K_{av}$ values was $1.5 \times 10^8$.

Example 4

Porous cellulose beads were obtained in the same manner and conditions as in Example 1 except that the temperature of cellulose slurry and the temperature of 1,2-dichlorobenzene were 4° C. As a result, a particle median diameter of the obtained beads was 96.3 µm. A crosslinking reaction was conducted in the same manner as in Example 1, and $K_{av}$ was calculated. $K_{av}$ value for the marker molecular weight of 67000 was 0.377, $K_{av}$ value for the marker molecular weight of 115000 was 0.335, $K_{av}$ value for the marker molecular weight of 440000 was 0.179, and $K_{av}$ value for the marker molecular weight of 660000 was 0.146. The exclusion limit molecular weight calculated from these $K_{av}$ values was $2.4 \times 10^6$.

FIG. 3 shows the particle diameter distributions in Example 1 to Example 4. The bead diameter decreases as the beads formation temperature rises. By controlling the beads formation temperature, the particle diameter could be easily controlled. FIG. 4 shows $K_{av}$ values in Example 1 to Example 4. The $K_{av}$ value and the exclusion limit molecular weight could be controlled by the beads formation temperature. The $K_{av}$ value indicates the diffusion behavior of the marker protein into beads. The larger the $K_{av}$ value is, the more easily the protein diffuses into the beads. The protein diffusion behavior reflects the pore size of beads, and a larger $K_{av}$ value indicates a larger pore size. Therefore, Example 1 to Example 4 demonstrate that the pore size of beads can be controlled by the beads formation temperature.

Example 5

8.65 g of powdery cellulose was dispersed in 60 g of water, and retained at 4° C. Then, 27 g of 31.9 wt % sodium hydroxide aqueous solution was added and stirred. Porous cellulose beads were obtained in the same manner and conditions as in Example 4 except that after stirring for 20 minutes, 77 g of water was added so that the concentration of sodium hydroxide was 5.0 wt %, and concentration of cellulose was 5.0 wt %. As a result, a particle median diameter of the obtained beads was 83.0 µm.

Comparative Example 1

Porous cellulose beads were obtained in the same manner and conditions as in Example 1 except that 8.65 g of powdery cellulose was dispersed in 128 g of water, and retained at 15° C., and then 35 g of 34.5 wt % sodium hydroxide aqueous solution was added so that the concentration of sodium hydroxide was 7 wt %. As a result, the obtained cellulose was not in the shape of beads as shown in FIG. 2.

Comparative Example 2

8.65 g of powdery cellulose was dispersed in 112 g of water, and retained at 4° C., and then 51 g of 30. 3 wt % sodium hydroxide aqueous solution was added so that the concentration of sodium hydroxide was 9 wt %, and the concentration of cellulose was 5.0 wt %. The obtained cellulose slurry at 4° C. was dispersed in 890 g of 1,2-dichlorobenzene containing 9.2 g of sorbitan monooleate to form a cellulose droplet dispersion. The cellulose droplet dispersion was put into a cylindrical container having an inner diameter of 85 mm. A two-stage turbine blade having a blade diameter of 45 mm was used for stirring, and the interval of blades was set at 75 mm. The dispersion was stirred at 600 rpm for 10 minutes, and 150 mL of methanol was added to obtain cellulose in the form of beads. This method is the same condition as in WO2012-1212158. As a result, a particle median diameter of the obtained beads was 111.0 µm. A crosslinking reaction was conducted in the same manner as in Example 1, and $K_{av}$ was calculated. $K_{av}$ value for the marker molecular weight of 12400 was 0.518, $K_{av}$ value for the marker molecular weight of 67000 was 0.356, $K_{av}$ value for the marker molecular weight of 115000 was 0.311, and $K_{av}$ value for the marker molecular weight of 440000 was 0.152. The exclusion limit molecular weight calculated from these $K_{av}$ values was $2.1 \times 10^6$. The $K_{av}$ value and the exclusion limit molecular weight of the obtained beads were smaller than the $K_{av}$ value and the exclusion limit molecular weight of the beads obtained in the conditions of Example 1 to Example 4.

Evaluation Method of First Embodiment

<Crosslinking of Cellulose Beads>

40 mL of porous cellulose beads obtained in each Example was moved to a reaction vessel, and 24.4 mL of a 2 N NaOH aqueous solution (prepared from NaOH available from NACALAI TESQUE, INC., and distilled water) was added. The temperature was adjusted to 40° C. Then, 24.4 mg of sodium borohydride, and 6.0 mL of Denacol EX-314 (available from Nagase ChemteX Corporation) containing glycerol polyglycidyl ether as a crosslinking agent were added, and stirred at 40° C. for 5 hours. After the reaction, the beads were washed with distilled water of 20 times or more of the volume of the beads under suction filtration to obtain crosslinked cellulose beads.

<Measurement of Gel Distribution Coefficient ($K_{av}$)>

(1) Column Packing

The porous cellulose beads were dispersed in RO water and degassed for 1 hour. The degassed porous cellulose beads or adsorbent were packed in a column (Tricorn 10/300 available from GE Healthcare Japan) at a linear velocity of 105 cm/h. Thereafter, the eluent at pH 7.5 (129 mL) was allowed to run through the column at linear velocity of 26 cm/h.

(2) Addition of Marker

As the marker, those listed below were used.

Blue Dextran 2000 (available from Pharmacia Fine Chemicals)

Cytochrome C (available from Wako Pure Chemical Industries, Ltd.), molecular weight 12400

Bovine Serum Albumin (available from Wako Pure Chemical Industries, Ltd.), molecular weight 67000

IgG derived from human (available from SIGMA), molecular weight 115000

Ferritin (available from SIGMA), molecular weight 440000

Thyroglobulin (available from SIGMA), molecular weight 660000

While the eluent was allowed to run through the column at linear velocity of 26 cm/h, each 12 μL of the aforementioned markers diluted into 5 mg/mL with a buffer at pH 7.5 was injected. The concentration of the marker was finely adjusted each time.

(3) Measurement

DGU-20A3, SCL-10A, SPD-10A, LC-10AD, SIL-20AC and CTO-10AC (each available from SHIMADZU Corporation) were used as measuring instruments, and LCsolution was used as measurement software. 50 mL graduated cylinder was used for measuring the liquid amount.

UV monitoring and measurement of the liquid amount started at the same time with injection of markers.

1) The liquid amount corresponding to the first peak of blue dextran was made as $V_0$ (mL).

2) The liquid amount corresponding to the peak of each marker was made as $V_R$ (mL).

3) The total volume of the porous cellulose beads or the adsorbent in the column was made as $V_t$ (mL).

4) Calculation

The distribution coefficient ($K_{av}$) of each marker was calculated by following formula.

$$K_{av}=(V_R-V_0)/(V_t-V_0)$$

5) Calculation of the Maximum Pore Size $K_{av}$ of each marker and the logarithm of the molecular weight were plotted, and the slope and the intercept of following formula were determined from the part showing linearity.

$$K_{av}=k \times L_n(\text{molecular weight})+b$$

Then, the molecular weight when $K_{av}$ was 0, namely, the exclusion limit molecular weight was determined from the determined slope and intercept.

2. Examples Regarding Improvement in Carrier for Ligand Immobilization (Second Embodiment)

Next, examples regarding the improvement in the carrier for ligand immobilization (second embodiment) is described. The physical properties of the cellulose porous beads, the crosslinked beads (hereinafter, these also collectively referred to as sample beads), and the adsorbent obtained by binding a ligand to the crosslinked beads, used or obtained in the following examples regarding the second embodiment were determined in the following manner.

I: Exclusion Limit Molecular Weight (1) Column Packing Operation

The sample beads were dispersed in RO water (reverse osmosis membrane purified water) and degassed for 1 hour. The degassed sample beads were packed in a column (Tricorn 10/300 available from GE Healthcare Japan) at a linear velocity of 105 cm/h. Thereafter, eluent at pH 7.5 (129 mL) was allowed to run through the column at linear velocity of 26 cm/h.

(2) Markers

Blue Dextran 2000 (available from Pharmacia Fine Chemicals)

Thyroglobulin (available from SIGMA), MW 660,000

Ferritin (available from SIGMA), MW 440,000

IgG derived from human (available from SIGMA), MW 115,000

Bovine Serum Albumin (available from Wako Pure Chemical Industries, Ltd.), MW 67,000

Cytochrome C (available from Wako Pure Chemical Industries, Ltd.), MW 12,400

Bacitracin (available from Wako Pure Chemical Industries, Ltd.), MW 1,400

(3) Measuring Instruments and Software

Names of instruments: DGU-20A3, SCL-10A, SPD-10A, LC-10AD, SIL-20AC, CTO-10AC (each available from SHIMADZU Corporation)

Name of software: LCsolution (4) Measurement

While the eluent was allowed to run through the column at a linear velocity of 26 cm/h, each 12 μL of the aforementioned markers diluted into 5 mg/mL with a buffer at pH 7.5 was injected. The concentration of the marker was finely adjusted each time. UV monitoring and measurement of the liquid amount started at the same time with injection of markers.

a) The liquid amount corresponding to the first peak of blue dextran was made as $V_0$ (mL).

b) The liquid amount corresponding to the peak of each marker was made as $V_R$ (mL).

c) The total volume of the sample beads in the column was made as $V_t$ (mL).

(5) Calculation

The gel phase distribution coefficient ($K_{av}$) of each marker was calculated according to the following formula.

$$K_{av}=(V_R-V_0)/(V_t-V_0)$$

$K_{av}$ of each marker and the logarithm of the molecular weight were plotted, and the slope and the intercept of following formula were determined from the part showing linearity.

$$K_{av}=k \times L_n(\text{molecular weight})+b$$

Then, the molecular weight at $K_{av}$ of 0 was determined from the determined slope and intercept, and the result was taken as the exclusion limit molecular weight.

II: Shrinkage Rate at Shrinking and Crosslinking Reaction

Using the total amounts of the cellulose porous beads before and after the shrinking and crosslinking reaction, the sum total of the gel volume was calculated in the following method. The gel volume $V_1$ of the polysaccharide porous beads before shrinking and crosslinking of the polysaccharide porous beads, and the gel volume $V_2$ of the polysaccharide porous beads after shrinking and crosslinking of the polysaccharide porous beads were determined.

(Measurement Method of Gel Volume)

The reaction solution before shrinking and crosslinking reaction or after shrinking and crosslinking reaction was washed, and replaced with RO water, and thus a sample slurry was prepared (the gel volume concentration approximately 30-70% by volume). The slurry was added to a 50 mL centrifugal tube, and the centrifugal tube was fixed on a small vibrator (VIBRATORY PACKER, VP-4D available from SINFONIA TECHNOLOGY), and vibration was applied at temperature 25° C. until the beads volume no longer changed. Then, the gel volumes $V_1$, $V_2$ were mea- III: 5% Dynamic Binding Capacity (1) Preparation of Solution The following solutions from A to E and neutralization solution were prepared, and they were defoamed before being used.

Solution A: PBS buffer at pH 7.4 was prepared by using "Phosphate buffered saline" available from Sigma and RO water (reverse osmosis membrane purified water).

Solution B: 35 mM sodium acetate aqueous solution at pH 3.5 was prepared by using acetic acid, sodium acetate and RO water.

Solution C: 1 M acetic acid aqueous solution was prepared by using acetic acid and RO water.

Solution D: An IgG aqueous solution at concentration of 1 mg/mL was prepared by using Gammagard (polyclonal antibody) available from Baxter, and the aforementioned solution A.

Solution E: 6 M urea aqueous solution was prepared by using urea and RO water.

Neutralization solution: 2 M tris(hydroxymethyl)aminomethane was prepared by using tris(hydroxymethyl)aminomethane and RO water.

(2) Packing, Preparation

AKTA explorer 100 (available from GE Healthcare) was used as an apparatus for column chromatography. 3 mL of an adsorbent sample (in which a ligand is bound to cross-linked beads) was added in a column having diameter of 0.5 cm and a height of 15 cm and packed by allowing 0.2 M NaCl aqueous solution (in RO water) to run through the column at a linear velocity of 230 cm/h for 15 minutes. 15 mL sampling tubes were set on a fraction collector, and tubes for sampling eluates were preliminarily charged with neutralization solution.

(3) Purification of IgG 15 mL of solution A was allowed to run through the column and then 150 mL of solution D was allowed to run though. Then, after allowing 21 mL of solution A to run through, 12 mL of solution B was allowed to run through to elute IgG. Then, 6 mL of solution C, 6 mL of solution E, and 15 mL of solution A were allowed to run through. The flow rate of each liquid was 1 mL/min so that the contact time with the adsorbent was 3 minutes.

(4) Dynamic Binding Capacity

The dynamic binding capacity (5% DBC) of IgG was determined from the IgG amount adsorbed to the adsorbent before 5% breakthrough of IgG and the volume of the adsorbent.

IV: 20% Compressive Stress (1) Preparation of Sample

Pure water was added to sample beads to prepare a slurry (concentration about 50% by volume). Homogenizing and defoaming operation consisting of homogenization by stirring of the slurry, and the subsequent defoaming under reduced pressure for not less than 30 minutes was repeated for three times to obtain efoamed slurry. Separately from this operation, the homogenizing and defoaming operation was conducted for not less than 90 minutes while the object to be treated was changed to pure water to obtain defoamed water.

(2) Preparation of Beads Packing Syringe

A disposable filter (pore diameter 5.00 µm, hydrophilic) was attached to the tip end of disposer syringe of 5 mL with a lure lock (trade name: NORM-JECT) available from HANKE SASS WOLF. A piston of the syringe was removed, and about 3 mL of defoamed water was introduced from the rear end side of the syringe. Before the defoamed water falls below the marked line of 0 mL, defoamed slurry was introduced. An aspirator was connected on the secondary side of the disposable filter, and the defoamed slurry was aspirated with care so that the liquid level did not fall below the beads level. Aspiration was stopped when the liquid level lowered to about 0.5 mL above the beads level. The subsequent operations were conducted while the defoamed water was appropriately added so that the liquid level did not fall below the beads level. The defoamed slurry was added or beads were removed under vibration and the beads level was adjusted to the marked line of 3 mL, and it was checked that the beads level did not lower even when vibration was applied. Defoamed water was added slowly until the defoamed water spilled over in such a manner that the beads did not swirl around, and a piston was inserted with care so that foams were not included (beads packing syringe).

(3) Measurement

A 10K load cell was attached to a FUDOH RHEO METER available from RHEOTECH, and the displacement rate was set at 2 cm/MIN of the dial, and the beads packing syringe was set, and displacement of the piston started. The relationship between the displacement and the stress was recorded, and 20% compressive stress was determined according to the following formula.

20% compressive stress=stress when packing beads are compressed by 20% stress directly before piston reaches beads level V: Linear Velocity of Critical Compression (1) Column Packing Operation Sample beads (89.5 mL) were dispersed in RO water, and packed in a column (available from MILLIPORE, inner diameter 2.2 cm) at a linear velocity of 300 cm/h.

(2) Measurement

The column was loaded on AKTApilot (available from GE Healthcare), and RO water was allowed to run though at flow rate of 5 mL/min (linear velocity 79 cm/hr). Subsequently, the flow rate was increased by 5 mL/min stepwise. Linear velocity of critical compression was defined as the linear velocity at the time when the column inlet pressure continuously increases and the liquid could not run through (in this test, at the time when the inlet pressure exceeded 2 MPa).

Production Example 1

8.65 g of powdery cellulose (pharmacopoeia cellulose "PH-F20JP" available from Asahi Kasei Chemicals Corporation) was dispersed in 112 g of water, and retained at 4° C. Then, 35 g of 34.5 wt % sodium hydroxide aqueous solution was added and stirred. After stirring for 20 minutes, 16 g of water was added so that the concentration of the sodium hydroxide was 7.0 wt % and the temperature was raised to 15° C. The temperature of 890 g of 1,2-dichlorobenzene solution containing 9.2 g of sorbitan monooleate was kept at 15° C., and the cellulose micro dispersion obtained above was dispersed in this solution. The dispersion was put into a cylindrical container having an inner diameter of 85 mm (hereinafter, referred to as a first container) equipped with a two-stage turbine blade having a blade diameter of 45 mm and an interval of blades of 75 mm, and the dispersion was stirred at a speed of 600 rpm for 10 minutes. Then, 150 mL of methanol was added to obtain cellulose in the form of beads. The obtained cellulose beads were washed with methanol, and then washed with water. The obtained cellulose beads were classified by using a mesh with an opening of sieve of 38 μm and a mesh with an opening of sieve of 90 μm, and cellulose particles within the range of 38 μm to 90 μm were collected.

The obtained cellulose porous beads were replaced with 2-methyl-2-propanol, and freeze-dried, and then analyzed by a scanning electron microscope (S-800 available from Hitachi, Ltd., hereinafter referred to as SEM), and it was confirmed that the beads were porous beads. The exclusion limit molecular weight calculated from the gel distribution coefficient ($K_{av}$) of the obtained beads was $6.0 \times 10^{10}$.

Example 6

(1) Shrinking and Crosslinking Step 100 mL of gel of cellulose porous beads (water-washed product) obtained in Production example 1 was placed on a glass filter, and solvent replacement operation of repulping with ethanol, and removing the ethanol by aspiration was repeated for four times. The amount of ethanol was 233 mL for the first to third times of the solvent replacement operation, and 167 mL for the fourth time of the solvent replacement operation. After the solvent replacement operation, the beads were moved to a cylindrical container having an inner diameter of 85 mm, equipped with a paddle blade of 39 mm in blade diameter (hereinafter, referred to as a second container), and the total volume was adjusted to 149 mL by adding the same solvent, and then the temperature was raised to 40° C. Further, 80 mL of epichlorohydrin was added, and stirred at a number of revolutions of 200 rpm for 30 minutes. Then, a mixture consisting of 10 mL of 17 M NaOH aqueous solution and 86 mL of water was added, and stirred at a number of revolutions of 350 rpm for one hour and 30 minutes, and thus cellulose porous beads were shrunk and crosslinked (the reaction refers to a shrinking and crosslinking main reaction). Epichlorohydrin concentration in the shrinking and crosslinking main reaction solution was 24.6% by volume, the organic solvent proportion (ethanol rate) was 0.61, NaOH concentration was 0.70 M, and cellulose porous beads concentration (slurry concentration) was 30.8% by volume. After conducting an additional treatment of adding 9.6 mL of 17 M NaOH aqueous solution and stirring at a number of revolutions of 350 rpm for 1.5 hours three times, the reaction solution was filtered, and the residue was washed with 20% ethanol water, followed by water to obtain intermediate crosslinked beads. The shrinkage rate by the shrinking and crosslinking step was determined, and shown in the following Table 1.

(2) Additional Crosslinking Step

Water was added to the whole of the obtained intermediate crosslinked beads to adjust the entire volume to 117 mL, and moved to the second container used in the shrinking and crosslinking step, and then the temperature was raised to 40° C. Then, 38 g of sodium sulfate was added, and stirred at a number of revolutions of 150 rpm for 10 minutes, and then 33 mL of epichlorohydrin was added, and stirred at a number of revolutions of 250 rpm for 10 minutes. Then, 21 mL of 17 M NaOH aqueous solution was added, and stirred at a number of revolutions of 300 rpm for 2.5 hours, and eventually 5.1 mL of 17 M NaOH aqueous solution was added and further stirred for 2.5 hours. The reaction solution was filtered, and the residue was washed with water to obtain crosslinked beads. The whole of the obtained crosslinked beads were put into a glass Erlenmeyer flask, and diluted with RO water so that the total amount was 200 mL. Then, the opening was lidded with two sheets of aluminum foil, and the flask was heated at 127° C. for 60 minutes in an autoclave, and thus the remaining epoxy groups were substituted by glyceryl groups. After allowing to cool to room temperature, the beads were washed on a glass filter with 200 mL of RO water. The beads after autoclaving were classified by using a mesh with an opening of sieve of 38 μm and a mesh with an opening of sieve of 90 μm to collect crosslinked beads within the range of 38 μm to 90 μm.

(3) Preparing Step of Protein A

Referring to WO2012/133349, as orientation-controlled protein A, a connected body of five modified-C domains as described in WO2012/133349 was prepared.

(4) Ligand Immobilizing Step 3.5 mL of the crosslinked beads obtained in the additional crosslinking step were introduced in a centrifugal tube, and RO water was added so that the total amount was 6 mL. The centrifugal tube was attached on a mixing rotor (MIX ROTOR MR-3 available from AS ONE Corporation) at 25° C., and stirred. Next, sodium periodate was dissolved in RO water, and 2.0 mL of 11.16 mg/mL of sodium periodate aqueous solution was added and stirred at 25° C. for 1 hour. Following the reaction, the beads were washed with RO water on a glass filter (11GP100 available from SHIBATA CO., LTD.) until the electric conductivity of the filtrate was not more than 1 μS/cm to obtain formyl group-containing crosslinked beads. The electric conductivity of the washing filtrate was measured by a conductivity meter (ECTester10 Pure+available from EUTECH INSTRUMENTS).

On a glass filter (11GP100 available from SHIBATA CO., LTD.), 3.5 mL of the obtained formyl group-containing crosslinked porous cellulose beads were replaced with 0.6 M citrate buffer (in RO water) at pH 12. Using 0.6 M citrate buffer at pH 12, the formyl group-containing crosslinked porous cellulose beads after replacement were put into a centrifugal tube, and the liquid amount was adjusted so that the total volume was 7.5 mL. 0.98 g of an aqueous solution containing orientation-controlled protein A obtained in the protein A preparing step (concentration of protein A is 53.8 mg/mL) was added thereto, and then allowed to react under stirring at 6° C. for 23 hours by using a MIX ROTOR (MIX ROTOR MR-3 available from AS ONE Corporation).

Thereafter, the reaction solution was collected (reaction solution 1), and replaced with 0.1 M sodium citrate aqueous solution (in RO water) at pH 8, and stirred at 6° C. for 4 hours by using a MIX ROTOR (MIX ROTOR MR-3 available from AS ONE Corporation). Subsequently, 1.93 mL of a dimethylamine borane aqueous solution (in RO water) in a concentration of 5.5% by mass was added and stirred at 6° C. for 1 hour. Then, the reaction temperature was raised to 25° C., and allowed to react at 25° C. for 18 hours under stirring by using a MIX ROTOR (MIX ROTOR MR-3 available from AS ONE Corporation). After reaction, the reaction solution was collected (reaction solution 2). UV absorbance of the maximum absorbance around 278 nm of the reaction solutions 1 and 2 was measured, and the measured value was subtracted from the loaded ligand amount to calculate the immobilized amount of protein A. The result is shown in Table 1.

The beads after reaction was washed with RO water in an amount of three times the volume of the beads on the glass filter (11GP100 available from SHIBATA CO., LTD.). Subsequently, 0.1 N citrate aqueous solution (in RO water) in an amount of three times the volume was added, and 0.1 N citric acid aqueous solution (in RO water) was added to the beads so that the total amount was not less than 30 mL, and these were put into a centrifugal tube, and thus acid washing was conducted at 25° C. for 30 minutes under stirring.

After acid washing, the beads were washed with RO water in an amount of three times the volume of the beads on the glass filter (11GP100 available from SHIBATA CO., LTD.), and then an aqueous solution (in RO water) containing 0.05 M sodium hydroxide and 1 M sodium sulfate in an amount of three times the volume was added. Then, aqueous solution containing 0.05 M sodium hydroxide and 1 M sodium sulfate was added so that the total amount was not less than 30 mL, and these were put into a centrifugal tube, and thus alkali washing was conducted at room temperature for 30 minutes under stirring.

After alkali washing, the beads were washed with RO water in an amount of 20 times the volume of the beads on the glass filter (11GP100 available from SHIBATA CO., LTD.), and then 0.1 N sodium citrate aqueous solution (in RO water) in an amount of three times the beads was added. After confirming that the filtrate was neutral, the beads were washed with RO water until the electric conductivity of the washing filtrate was not more than 1 µS/cm to obtain an adsorbent in which the objective orientation-controlled protein A was immobilized. The electric conductivity of the washing filtrate was measured by a conductivity meter (ECTester10 Pure+available from EUTECH INSTRUMENTS).

The linear velocity of critical compression and the 20% compressive stress of the crosslinked beads (after the additional crosslinking step) obtained in the manner as described above, and the 5% dynamic binding capacity (contact time 3 minutes) of the adsorbent were measured. The linear velocity of critical compression of the crosslinked beads was 1658 cm/hr. The remaining results are shown in Table 1.

Examples 7-8

The same operation as in Example 6 was conducted except that ethanol used in the shrinking and crosslinking step was changed to each organic solvent shown in Table 1, and the organic solvent proportion, the epichlorohydrin concentration, the NaOH concentration, and the slurry concentration (cellulose porous beads concentration) in the shrinking and crosslinking step were changed to the values shown in Table 1. The results are shown in Table 1.

TABLE 1

|  | Example 6 | Example 7 | Example 8 |
| --- | --- | --- | --- |
| Organic solvent*[1] | Ethanol | Ethanol | DMSO |
| Concentration of epichlorohydrin (volume %) | 24.6 | 12.3 | 12.3 |
| Organic solvent proportion | 0.61 | 0.59 | 0.53 |
| Concentration of NaOH (M) | 0.70 | 0.60 | 0.60 |
| Concentration of slurry (volume %) | 30.8 | 30.8 | 30.8 |
| Shrinkage rate at shrinking and crosslinking step (%) | 36.7 | 22.4 | 26.8 |
| 20% compressive stress (MPa) | 0.112 | 0.072 | 0.096 |
| Immobilized amount of protein A (mg/mL - gel) | 13.4 | 12.6 | 12.8 |
| 5% dynamic binding capacity (mg/mL - gel) | 41.7 | 44.4 | 43.7 |

*[1]DMSO = Dimethyl sulfoxide

Examples 9-10, Comparative Example 3

(1) Shrinking and Crosslinking Step

On a glass filter, 15 mL of gel of cellulose porous beads (water washed product) obtained in Production example 1 was placed, and a solvent replacement operation of repulping with 15 mL of a specific solvent shown in Table 2, and removing the specific solvent by aspiration was repeated three times. After the solvent replacement operation, the whole of the gel was put into a centrifugal tube, and the volume was adjusted so that the total amount was 17.5 mL by adding the same specific solvent, and further 8.7 mL of epichlorohydrin was added and stirred overnight. Subsequently, 10.3 mL of water and 2.1 mL of 17 M NaOH aqueous solution were added, and stirred at temperature of 40° C. for one hour and 30 minutes to cause shrinking and crosslinking of the cellulose porous beads (shrinking and crosslinking main reaction). The epichlorohydrin concentration, the organic solvent proportion, the NaOH concentration and the cellulose porous beads concentration (slurry concentration) in the shrinking and crosslinking main reaction solution are shown in Table 2 below. Then, 1.05 mL of 17 M NaOH aqueous solution was added, and stirred for 1.5 hour, and then additional treatment of adding 1.05 mL of 17 M NaOH aqueous solution and stirring for 2 hours was conducted, and then they were filtered, and the residue was washed with 20% specific solvent aqueous solution, followed by water to obtain intermediate crosslinked beads. The shrinkage rate by the shrinking and crosslinking step was determined, and shown in Table 2 below.

(2) Additional Crosslinking Step

The whole of the obtained intermediate crosslinked beads were put into a centrifugal tube, and the entire volume was adjusted to 17.5 mL by addition of water, and then the temperature was raised to 40° C. Then, 5.67 g of sodium sulfate, 4.95 mL of epichlorohydrin, and 3.14 mL of 17 M NaOH aqueous solution were added, and stirred at temperature 40° C. for 2.5 hours, and finally 0.76 mL of 17 M NaOH aqueous solution was added and stirred for another 2.5 hours. The reactant was filtered, and the residue was washed with water to obtain crosslinked beads. The whole of the obtained crosslinked beads were put into a glass Erlenmeyer flask, and diluted with RO water so that the total volume was 50 mL, and then the opening was lidded with two sheets of aluminum foil, and the flask was heated at 127° C. for 60 minutes in an autoclave. After allowing to cool to room temperature, the beads were washed with 50 mL of RO water on a glass filter, to substitute the remaining epoxy groups with glyceryl groups. The beads after autoclaving were classified by using a mesh with an opening of sieve of 38 µm and a mesh with an opening of sieve of 90 µm, and an adsorbent within the range of 38 µm to 90 µm was collected.

(3) Preparing Step of Protein A

Referring to Examples of WO2011/118699, as modified protein A, a connected body of five modified-C domains having alkali resistance as described in WO2011/118699 was prepared.

(4) Ligand Immobilizing Step 5 mL of crosslinked porous cellulose beads obtained in the additional crosslinking step were introduced in a centrifugal tube, and RO water was added so that the total amount was 7.5 mL. The centrifugal tube was attached on a mixing rotor (MIX ROTOR MR-3 available from AS ONE Corporation) at 25° C. and stirred. Next, sodium periodate was dissolved in RO water, and 2.5 mL of 12.84 mg/mL of sodium periodate aqueous solution was added and stirred at 25° C. for 1 hour. After the reaction, the beads were washed with RO water on a glass filter (11GP100 available from SHIBATA CO., LTD.) until the electric conductivity of the filtrate was not more than 1 µS/cm to obtain formyl group-containing crosslinked porous cellulose beads. The electric conductivity of the washing filtrate was measured by a conductivity meter (ECTester10 Pure+available from EUTECH INSTRUMENTS).

5 mL of the obtained formyl group-containing crosslinked porous cellulose beads were replaced with 0.25 M citrate buffer (prepared by using trisodium citrate dihydrate and RO water) on a glass filter (11GP100 available from SHIBATA CO., LTD.). Using 0.25 M citrate buffer, the formyl group-containing crosslinked porous cellulose beads after replacement were put into a centrifugal tube, and the liquid amount was adjusted so that the total volume was 7.5 mL. 2.13 g of aqueous solution containing alkali resistant protein A obtained in the protein A preparing step (protein A concentration 70.3 mg/mL) was added thereto, and pH was adjusted to 12 with 0.08 N sodium hydroxide aqueous solution, and then allowed to react under stirring at 6° C. for 23 hours by using a MIX ROTOR (MIX ROTOR MR-3 available from AS ONE Corporation).

Thereafter, 2.4 M citric acid aqueous solution (prepared by using citric acid monohydrate and RO water) was added until pH of the reaction solution was 5, and stirred at 6° C. for 4 hours by using a MIX ROTOR (MIX ROTOR MR-3 available from AS ONE Corporation). Subsequently, 1.13 mL of a dimethylamine borane aqueous solution (in RO water) in concentration of 5.5% by mass was added and stirred at 6° C. for 1 hour, and then the reaction temperature was raised to 25° C., and allowed to react at 25° C. for 18 hours under stirring. After reaction, the reaction solution was collected, and UV absorbance of the maximum absorbance around 278 nm was measured, and the measured value was subtracted from the loaded ligand amount to calculate the immobilized amount of protein A.

In the subsequent steps, the beads after reaction were washed (acid washing, alkali washing, neutralization) by repeating the same operations as in the ligand immobilizing step in Example 6, and thus an adsorbent in which objective alkali resistant protein A was immobilized was obtained.

20% compressive stress of the crosslinked beads (after the additional crosslinking step) obtained in the manner as described above, and the amount of immobilized protein A per 1 mL of the adsorbent, and the 5% dynamic binding capacity (contact time 3 minutes) of the adsorbent were measured. The results are shown in Table 2.

TABLE 2

|  | Comparative Example 3 | Example 9 | Example 10 |
|---|---|---|---|
| Specific solvent | Water | Mixed solvent*1 | Ethanol |
| Concentration of epichlorohydrin (volume %) | 22.5 | 22.5 | 22.5 |
| Organic solvent proportion | 0 | 0.59 | 0.59 |
| Concentration of NaOH (M) | 1.19 | 1.19 | 1.19 |
| Concentration of slurry (volume %) | 38.9 | 38.9 | 38.9 |
| Shrinkage rate at shrinking and crosslinking step (%) | −5 | 16 | 37 |
| 20% compressive stress (MPa) | 0.048 | 0.092 | 0.14 |
| Immobilized amount of protein A (mg/mL - gel) | 15.0 | 15.9 | 12.7 |
| 5% dynamic binding capacity (mg/mL - gel) | 40.1 | 42.5 | 42.6 |

*2Mixed solvent of methanol/dimethyl sulfoxide = 1/1 (volume ratio)

Examples 11-17

The same operation as in Examples 9-10 was conducted except that the solvent used in the shrinking and crosslinking step was changed to those shown in Table 3. The results are shown in Table 3. The relationship between the shrinkage rate and the 20% compressive stress is shown in FIG. 5.

TABLE 3

| Specific solvent*1 | Example 11 Methanol | Example 12 Acetonitrile | Example 13 IPA | Example 14 DMSO | Example 15 DMA | Example 16 Acetone | Example 17 Dioxane |
|---|---|---|---|---|---|---|---|
| Concentration of epichlorohydrin (volume %) | 22.5 | 22.5 | 22.5 | 22.5 | 22.5 | 22.5 | 22.5 |
| Organic solvent proportion | 0.59 | 0.59 | 0.59 | 0.59 | 0.59 | 0.59 | 0.59 |
| Concentration of NaOH (M) | 1.19 | 1.19 | 1.19 | 1.19 | 1.19 | 1.19 | 1.19 |
| Concentration of slurry (volume %) | 38.9 | 38.9 | 38.9 | 38.9 | 38.9 | 38.9 | 38.9 |
| Shrinkage rate at shrinking and crosslinking step (%) | 10 | 14 | 40 | 43 | 60 | 23 | 23 |
| 20% compressive stress (MPa) | 0.072 | 0.072 | 0.124 | 0.18 | 0.272 | 0.092 | 0.096 |

*1IPA = Isopropanol, DMSO = Dimethyl sulfoxide, DMA = Dimethyl acetamide

Comparative Example 4

(1) First Crosslinking Step 20 mL of gel of the cellulose porous beads (water washed product) obtained in Production example 1 was placed on a glass filter, and repulped with RO water, and then RO water was removed by aspiration. The whole of the beads were put into a centrifugal tube, and 12.2 mL of 2 M NaOH aqueous solution was added and mixed. Further 6.6 mL of glycerol polyglycidyl ether (Denacol EX314 available from Nagase ChemteX Corporation) and 7.6 g of sodium sulfate were added, and stirred at temperature of 40° C. for 5 hours to cause crosslinking of the cellulose porous beads. Then, these were filtered, and the residue was washed with water to obtain intermediate crosslinked beads.

(2) Second Crosslinking Step

The whole of the obtained intermediate crosslinked beads were put into a centrifugal tube, and 12.2 mL of 2 M NaOH aqueous solution was added and mixed. Further, 6.6 mL of glycerol polyglycidyl ether and 7.6 g of sodium sulfate were added, and stirred at temperature of 40° C. for 5 hours, and then filtered, and the residue was washed with water to obtain crosslinked beads. The whole of the obtained crosslinked beads were put into a glass Erlenmeyer flask, and diluted with RO water so that the total amount was 50 mL, and then the opening was lidded with two sheets of aluminum foil, and the flask was heated at 127° C. for 60 minutes in an autoclave. After allowing to cool to room temperature, the beads were washed with 50 mL of RO water on a glass filter to substitute the remaining epoxy groups with glyceryl groups. The beads after autoclaving were classified by using a mesh with an opening of sieve of 38 μm and a mesh with an opening of sieve of 90 μm, and crosslinked beads within the range of 38 μm to 90 μm was collected. The shrinkage rate after crosslinking was 0%.

In the subsequent steps, (4) ligand immobilizing step was conducted in the same manner as in Examples 9-10, and thus an adsorbent in which objective alkali resistant protein A being immobilized was obtained.

20% compressive stress of the crosslinked beads (after the second crosslinking step) obtained in the manner as described above, and the amount of immobilized protein A per 1 mL of the adsorbent, and the 5% dynamic binding capacity (contact time 3 minutes) of the adsorbent were measured. The 20% compressive stress was 0.084 MPa, the immobilized amount was 14.8 mg/mL-gel, and the 5% dynamic binding capacity (DBC) was 22.0 mg/mL-gel.

INDUSTRIAL APPLICABILITY

The porous cellulose beads according to the first embodiment can be used as an adsorbent for various substances by addition of various substituents. The carrier for ligand immobilization according to the second embodiment can be turned into an adsorbent by immobilizing a ligand.

The invention claimed is:

1. A carrier for ligand immobilization, obtained by a process comprising shrinking polysaccharide porous beads such that a shrinkage rate is not less than 10%, and crosslinking the polysaccharide porous beads, wherein Shrinkage rate (%)=$(1-V_2/V_1)\times 100$ wherein $V_1$ represents a gel volume of the polysaccharide porous beads before the shrinking, and $V_2$ represents a gel volume of the polysaccharide porous beads after the shrinking.

2. The carrier according to claim 1, wherein the shrinking comprises contacting the polysaccharide porous beads into contact with a water-soluble organic solvent and alkali water.

3. The carrier according to claim 2, wherein the shrinking is carried out in the presence of a crosslinking agent such that the polysaccharide porous beads are crosslinked during the shrinking, or the crosslinking is carried out after the shrinking such that shrunk polysaccharide porous beads obtained by the shrinking are crosslinked.

4. The carrier according to claim 3, wherein the process further comprises, after the crosslinking, additionally contacting the polysaccharide porous beads with a crosslinking agent and alkali water at least one time.

5. The carrier according to claim 1, wherein the polysaccharide porous beads comprise a polysaccharide which is cellulose or agarose.

6. The carrier according to claim 2, wherein the water-soluble organic solvent is at least one selected from the group consisting of an alcohol solvent, a sulfoxide solvent, an amide solvent, a ketone solvent, and an ether solvent.

7. The carrier according to claim 4, wherein an alcohol solvent is not used in the additional contacting crosslinking.

8. An adsorbent, obtained by immobilizing a ligand on the carrier according to claim 1.

9. The adsorbent according to claim 8, wherein the ligand is an affinity ligand.

10. The adsorbent according to claim 9, wherein the affinity ligand is protein A, protein G, or protein L.

11. A method for purifying an antibody by affinity chromatography, the method comprising:
contacting a source material with the adsorbent according to claim 9, such that an antibody is adsorbed on the adsorbent;
washing the antibody adsorbed on the adsorbent;
adding an eluent such that the antibody is liberated from the adsorbent; and
collecting the liberated antibody from the eluent.

12. The carrier according to claim 1, wherein the polysaccharide porous beads have an exclusion limit molecular weight of $1.0\times10^5$ to $1.0\times10^{12}$.

13. The carrier according to claim 1, wherein the polysaccharide porous beads have an exclusion limit molecular weight of $1.0\times10^6$ to $1.0\times10^{11}$.

14. The carrier according to claim 2, wherein the water-soluble organic solvent is at least one selected from the group consisting of methanol, ethanol, propanol, dimethyl sulfoxide, dimethyl formamide, dimethyl acetamide, N-methylpyrrolidone, acetone, dioxane, and tetrahydrofuran.

15. The carrier according to claim 1, wherein the process comprises shrinking the polysaccharide porous beads such that the shrinkage rate is 10% to 60%.

16. The carrier according to claim 1, wherein the process comprises shrinking the polysaccharide porous beads such that the shrinkage rate is 20% to 50%.

17. The carrier according to claim 1, wherein the carrier has a 20% compressive stress of 0.06 MPa to 0.28 MPa.

18. The carrier according to claim 1, wherein the carrier has a 20% compressive stress of 0.072 MPa to 0.20 MPa.

19. The carrier according to claim 1, wherein the carrier has a 20% compressive stress of 0.092 MPa to 0.20 MPa.

20. The carrier according to claim 1, wherein the carrier has a particle diameter of 10 μm to 200 μm.

* * * * *

UNITED STATES PATENT AND TRADEMARK OFFICE
CERTIFICATE OF CORRECTION

PATENT NO. : 10,457,705 B2
APPLICATION NO. : 16/227688
DATED : October 29, 2019
INVENTOR(S) : Takahiro Okubo et al.

It is certified that error appears in the above-identified patent and that said Letters Patent is hereby corrected as shown below:

On the Title Page

Item (54) and in the Specification, Column 1, should read:
--PROCESS FOR PRODUCING POROUS CELLULOSE BEADS USING ALKALI AQUEOUS SOLUTION, CARRIER FOR LIGAND IMMOBILIZATION, AND ADSORBENT--

Signed and Sealed this
Thirty-first Day of December, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 291
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Lys Phe
    50                  55                  60

Asn Lys Asp Gln Gln Ser Ala Phe Tyr Glu Ile Leu Asn Met Pro Asn
65                  70                  75                  80

Leu Asn Glu Glu Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ala Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205
```

-continued

```
Leu Lys Asp Asp Pro Ser Gln Ser Ala Asn Leu Leu Ala Glu Ala Lys
    210             215                 220

Lys Leu Asn Asp Ala Gln Ala Pro Lys Ala Asp Asn Lys Phe Asn Lys
225             230             235                 240

Glu Gln Gln Asn Ala Phe Tyr Glu Ile Leu His Leu Pro Asn Leu Thr
            245                 250                 255

Glu Glu Gln Arg Asn Gly Phe Ile Gln Ser Leu Lys Asp Asp Pro Ser
            260             265                 270

Val Ser Lys Glu Ile Leu Ala Glu Ala Lys Lys Leu Asn Asp Ala Gln
    275                 280                 285

Ala Pro Lys
    290
```